(12) United States Patent
Roby et al.

(10) Patent No.: US 7,942,302 B2
(45) Date of Patent: May 17, 2011

(54) SURGICAL STAPLING DEVICE WITH COATED KNIFE BLADE

(75) Inventors: Mark S. Roby, Killingworth, CT (US);
Keith L. Milliman, Bethel, CT (US);
Anthony Dato, East Haven, CT (US);
Douglas J. Cuny, Bethel, CT (US);
Anthony Gaddy, Bridgeport, CT (US);
John J. Kennedy, Guilford, CT (US);
Nicholas Maiorino, Branford, CT (US);
Alan Byron Cabezas, Seymour, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 200 days.

(21) Appl. No.: 12/171,616

(22) Filed: Jul. 11, 2008

(65) Prior Publication Data
US 2008/0277448 A1   Nov. 13, 2008

Related U.S. Application Data

(63) Continuation of application No. 11/219,386, filed on Sep. 2, 2005, now abandoned, which is a continuation-in-part of application No. 11/158,860, filed on Jun. 22, 2005, now abandoned, which is a continuation of application No. 09/964,901, filed on Sep. 27, 2001, now Pat. No. 6,936,297.

(51) Int. Cl.
*A61B 17/068* (2006.01)
(52) U.S. Cl. ................. 227/175.1; 227/180.1
(58) Field of Classification Search ............... 227/175.1, 227/180.1; 606/41, 45; 427/2.28, 387
See application file for complete search history.

(56) References Cited

U.S. PATENT DOCUMENTS

| 3,388,847 | A | 6/1968 | Kasulin et al. |
|---|---|---|---|
| 3,552,626 | A | 1/1971 | Astafiev |
| 3,574,673 | A | 4/1971 | Schweiger et al. |
| 3,638,652 | A | 2/1972 | Kelley |
| 3,767,385 | A | 10/1973 | Slaney |
| 3,816,920 | A | 6/1974 | Sastri |
| 4,198,982 | A | 4/1980 | Fortner et al. |
| 4,207,898 | A | 6/1980 | Becht |
| 4,289,133 | A | 9/1981 | Rothfuss |
| 4,304,236 | A | 12/1981 | Conta et al. |
| 4,319,576 | A | 3/1982 | Rothfuss |
| 4,350,160 | A | 9/1982 | Kolesov et al. |
| 4,351,466 | A | 9/1982 | Noiles |
| 4,379,457 | A | 4/1983 | Gravener et al. |

(Continued)

FOREIGN PATENT DOCUMENTS
CA   908529   8/1972
(Continued)

OTHER PUBLICATIONS

European Search Report for EP 06018209, date of completion is Dec. 1, 2006 (3 pages).

*Primary Examiner* — Rinaldi I. Rada
*Assistant Examiner* — Michelle Lopez

(57) ABSTRACT

A surgical stapling device is disclosed for performing circular anastomoses. The surgical stapling device includes a handle portion, an elongated body portion and a head portion including an anvil assembly and a shell assembly. The surgical stapling device includes a knife blade possessing a lubricious coating which enhances the ability of the knife to cut through tissue and minimizes the knife sticking to tissue or other components of the surgical stapling device.

24 Claims, 33 Drawing Sheets

U.S. PATENT DOCUMENTS

| | | |
|---|---|---|
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,720,521 A | 1/1988 | Spielvogel et al. |
| 4,754,909 A | 7/1988 | Barker et al. |
| 4,806,430 A | 2/1989 | Spielvogel et al. |
| 4,817,847 A | 4/1989 | Redtenbacher et al. |
| 4,844,986 A | 7/1989 | Karakelle et al. |
| 4,873,977 A | 10/1989 | Avant et al. |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,181,416 A | 1/1993 | Evans |
| 5,185,006 A | 2/1993 | Williamitis et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,258,013 A | 11/1993 | Granger et al. |
| 5,261,920 A | 11/1993 | Main et al. |
| 5,266,359 A | 11/1993 | Spielvogel |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,437,656 A | 8/1995 | Shikani et al. |
| 5,456,948 A | 10/1995 | Mathisen et al. |
| 5,458,616 A | 10/1995 | Granger et al. |
| 5,533,982 A | 7/1996 | Rizk et al. |
| 5,534,609 A | 7/1996 | Lewis et al. |
| 5,536,582 A | 7/1996 | Prasad et al. |
| 5,639,008 A | 6/1997 | Gallagher et al. |
| 5,658,300 A | 8/1997 | Bito et al. |
| 5,669,918 A | 9/1997 | Balazs et al. |
| 5,685,474 A | 11/1997 | Seeber |
| 5,688,747 A | 11/1997 | Khan et al. |
| 5,702,387 A | 12/1997 | Arts et al. |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,736,251 A | 4/1998 | Pinchuk |
| 5,758,814 A | 6/1998 | Gallagher et al. |
| 5,799,857 A | 9/1998 | Robertson et al. |
| 5,801,057 A | 9/1998 | Smart et al. |
| 5,817,325 A | 10/1998 | Sawan et al. |
| 5,836,503 A | 11/1998 | Ehrenfels et al. |
| 5,839,639 A | 11/1998 | Sauer et al. |
| 5,853,745 A | 12/1998 | Darouiche |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,911,711 A | 6/1999 | Pelkey |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,985,355 A | 11/1999 | Walther et al. |
| 5,993,468 A | 11/1999 | Rygaard |
| 6,015,398 A | 1/2000 | Arimatsu et al. |
| 6,046,143 A | 4/2000 | Khan et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,248,117 B1 | 6/2001 | Blatter |
| 6,253,984 B1 | 7/2001 | Heck et al. |
| 6,258,107 B1 | 7/2001 | Balázs et al. |
| 6,264,086 B1 | 7/2001 | McGuckin, Jr. |
| 6,269,997 B1 | 8/2001 | Balázs et al. |
| 6,273,897 B1 * | 8/2001 | Dalessandro et al. ........ 606/139 |
| 6,279,809 B1 | 8/2001 | Nicolo |
| 6,296,893 B2 | 10/2001 | Heinz et al. |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,540,745 B1 | 4/2003 | Fairbourn et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,623,227 B2 | 9/2003 | Scott et al. |
| 6,626,921 B2 | 9/2003 | Blatter et al. |

| | | | |
|---|---|---|---|
| 6,629,630 B2 | 10/2003 | Adams | |
| 6,631,837 B1 | 10/2003 | Heck | |
| 6,632,227 B2 | 10/2003 | Adams | |
| 6,632,237 B2 | 10/2003 | Ben-David et al. | |
| 6,659,327 B2 | 12/2003 | Heck et al. | |
| 6,676,671 B2 | 1/2004 | Robertson et al. | |
| 6,681,979 B2 | 1/2004 | Whitman | |
| 6,685,079 B2 | 2/2004 | Sharma et al. | |
| 6,695,198 B2 | 2/2004 | Adams et al. | |
| 6,695,199 B2 | 2/2004 | Whitman | |
| 6,716,222 B2 | 4/2004 | McAlister et al. | |
| 6,716,233 B1 | 4/2004 | Whitman | |
| 6,742,692 B2 | 6/2004 | Hartwick | |
| 6,763,993 B2 | 7/2004 | Bolduc et al. | |
| 6,769,590 B2 | 8/2004 | Vresh et al. | |
| 6,769,594 B2 | 8/2004 | Orban, III | |
| 6,820,791 B2 | 11/2004 | Adams | |
| 6,827,246 B2 | 12/2004 | Sullivan et al. | |
| 6,840,423 B2 | 1/2005 | Adams et al. | |
| 6,866,178 B2 | 3/2005 | Adams et al. | |
| 6,872,214 B2 | 3/2005 | Sonnenschein et al. | |
| 6,874,669 B2 | 4/2005 | Adams et al. | |
| 6,884,250 B2 | 4/2005 | Monassevitch et al. | |
| 6,905,504 B1 | 6/2005 | Vargas | |
| 6,938,814 B2 | 9/2005 | Sharma et al. | |
| 2001/0000903 A1 | 5/2001 | Heck et al. | |
| 2001/0010320 A1 | 8/2001 | Bolduc et al. | |
| 2001/0054636 A1 | 12/2001 | Nicolo | |
| 2002/0020732 A1 | 2/2002 | Adams et al. | |
| 2002/0047036 A1 | 4/2002 | Sullivan et al. | |
| 2002/0063143 A1 | 5/2002 | Adams et al. | |
| 2002/0185516 A1 | 12/2002 | Heck et al. | |
| 2002/0185517 A1 | 12/2002 | Vresh et al. | |
| 2003/0019905 A1 | 1/2003 | Adams et al. | |
| 2003/0047582 A1 | 3/2003 | Sonnenschein et al. | |
| 2003/0057251 A1 | 3/2003 | Hartwick | |
| 2003/0065342 A1 | 4/2003 | Nobis et al. | |
| 2003/0073981 A1 | 4/2003 | Whitman et al. | |
| 2003/0089757 A1 | 5/2003 | Whitman | |
| 2003/0096545 A1 | 5/2003 | Payne | |
| 2003/0111507 A1 | 6/2003 | Nunez | |
| 2003/0127491 A1 | 7/2003 | Adams et al. | |
| 2003/0132267 A1 | 7/2003 | Adams et al. | |
| 2003/0144675 A1 | 7/2003 | Nicolo | |
| 2003/0147925 A1 | 8/2003 | Sawan et al. | |
| 2003/0178465 A1 | 9/2003 | Bilotti et al. | |
| 2003/0183671 A1 | 10/2003 | Mooradian et al. | |
| 2003/0192936 A1 | 10/2003 | Hartwick | |
| 2003/0192937 A1 | 10/2003 | Sullivan et al. | |
| 2003/0201301 A1 | 10/2003 | Bolduc et al. | |
| 2003/0218047 A1 | 11/2003 | Sharma et al. | |
| 2003/0222117 A1 | 12/2003 | Orban, III | |
| 2004/0092960 A1 | 5/2004 | Abrams et al. | |
| 2004/0092974 A1 | 5/2004 | Gannoe et al. | |
| 2004/0118896 A1 | 6/2004 | Sharma et al. | |
| 2004/0134964 A1 | 7/2004 | Adams et al. | |
| 2004/0153124 A1 | 8/2004 | Whitman | |
| 2004/0232198 A1 | 11/2004 | Adams et al. | |
| 2005/0051597 A1 | 3/2005 | Toledano | |
| 2005/0067454 A1 | 3/2005 | Vresh et al. | |
| 2005/0087580 A1 | 4/2005 | Orban, III | |
| 2005/0107813 A1 | 5/2005 | Gilete Garcia | |
| 2005/0116009 A1 | 6/2005 | Milliman | |
| 2005/0125009 A1 | 6/2005 | Perry et al. | |
| 2005/0143758 A1 | 6/2005 | Abbott et al. | |
| 2005/0145674 A1 | 7/2005 | Sonnenschein et al. | |
| 2005/0145675 A1 | 7/2005 | Hartwick et al. | |
| 2007/0060952 A1 * | 3/2007 | Roby et al. | 606/219 |

FOREIGN PATENT DOCUMENTS

| | | |
|---|---|---|
| DE | 1057729 | 5/1959 |
| DE | 3301713 | 11/1989 |
| EP | 0152382 | 8/1985 |
| EP | 0173451 | 3/1986 |
| EP | 0190022 | 8/1986 |
| EP | 282157 | 9/1988 |
| EP | 0494648 A2 | 7/1992 |
| EP | 0503689 | 9/1992 |
| EP | 0 627 474 A1 | 12/1994 |
| EP | 0 848 055 A1 | 6/1998 |
| EP | 878206 A2 | 6/1998 |
| EP | 1462129 A | 9/2004 |
| FR | 1461464 | 12/1966 |
| FR | 1588250 | 4/1970 |
| FR | 1136020 | 12/1979 |
| FR | 2443239 | 12/1979 |
| GB | 1185292 | 3/1970 |
| GB | 2016991 | 9/1979 |
| GB | 2070499 | 9/1981 |
| JP | 06-088025 | 3/1994 |
| NL | 7711347 | 10/1977 |
| WO | 8706448 | 11/1987 |
| WO | 8900406 | 1/1989 |
| WO | 9006085 | 6/1990 |
| WO | WO2004/009146 A | 1/2004 |

* cited by examiner

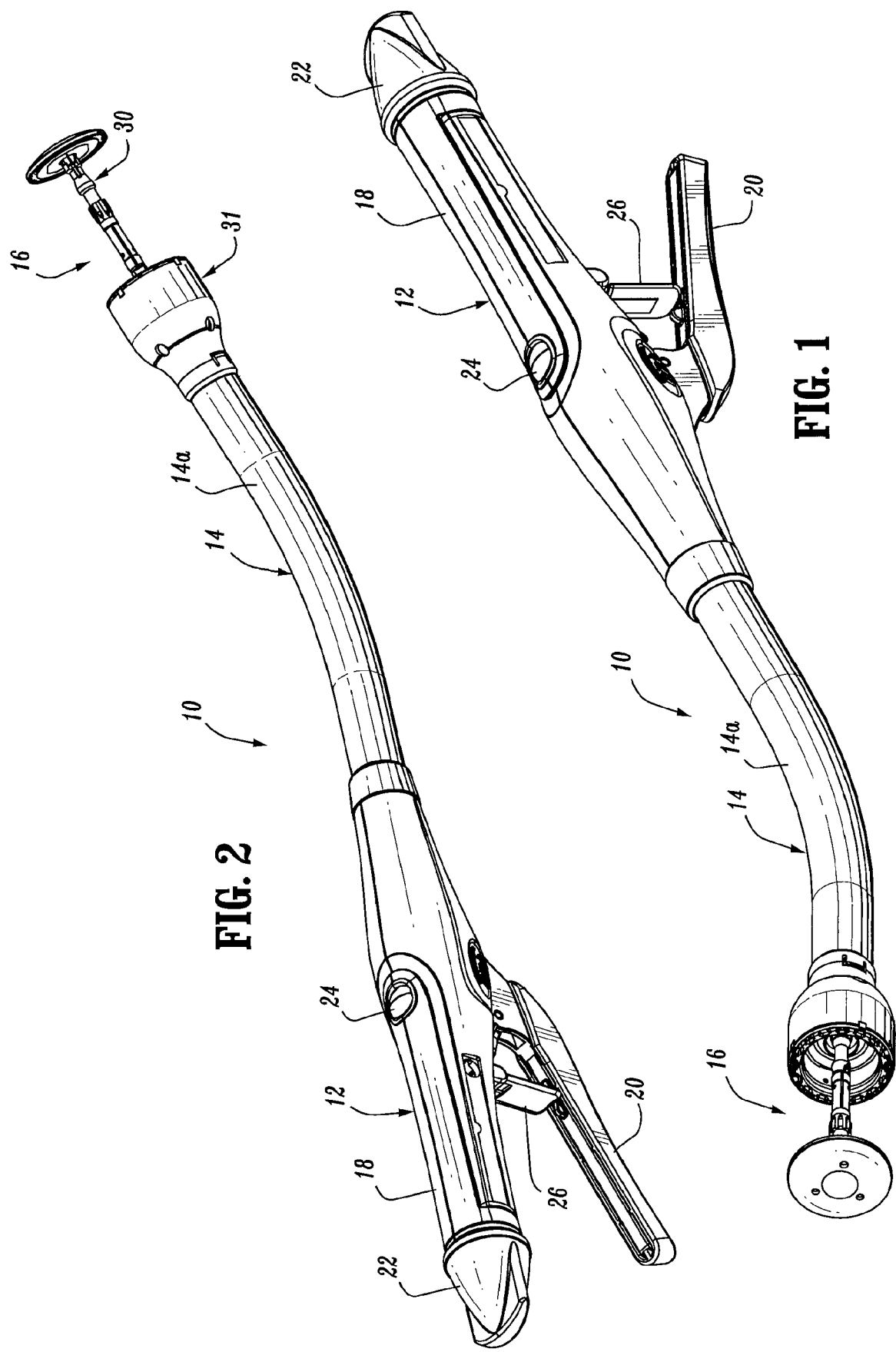

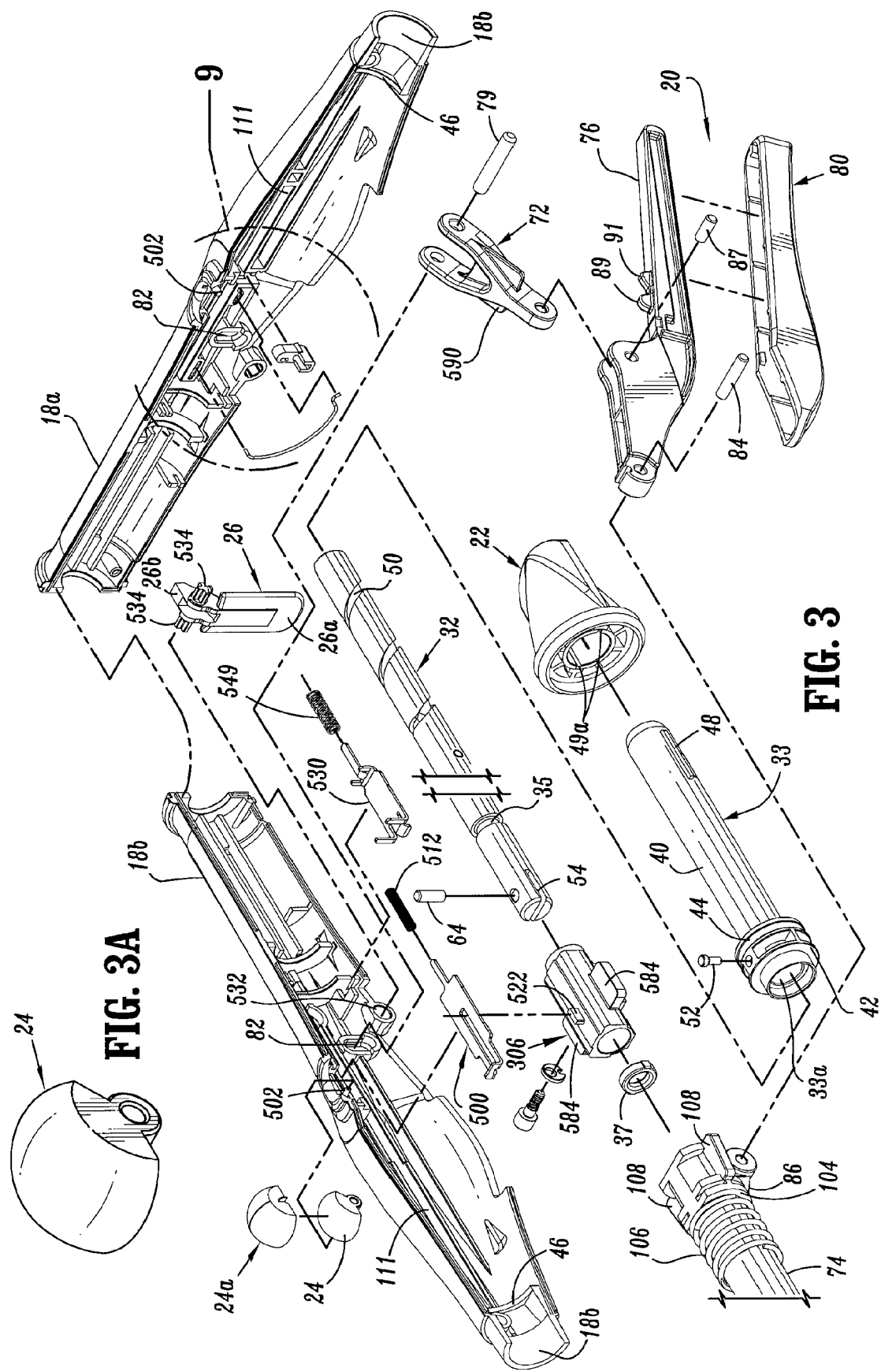

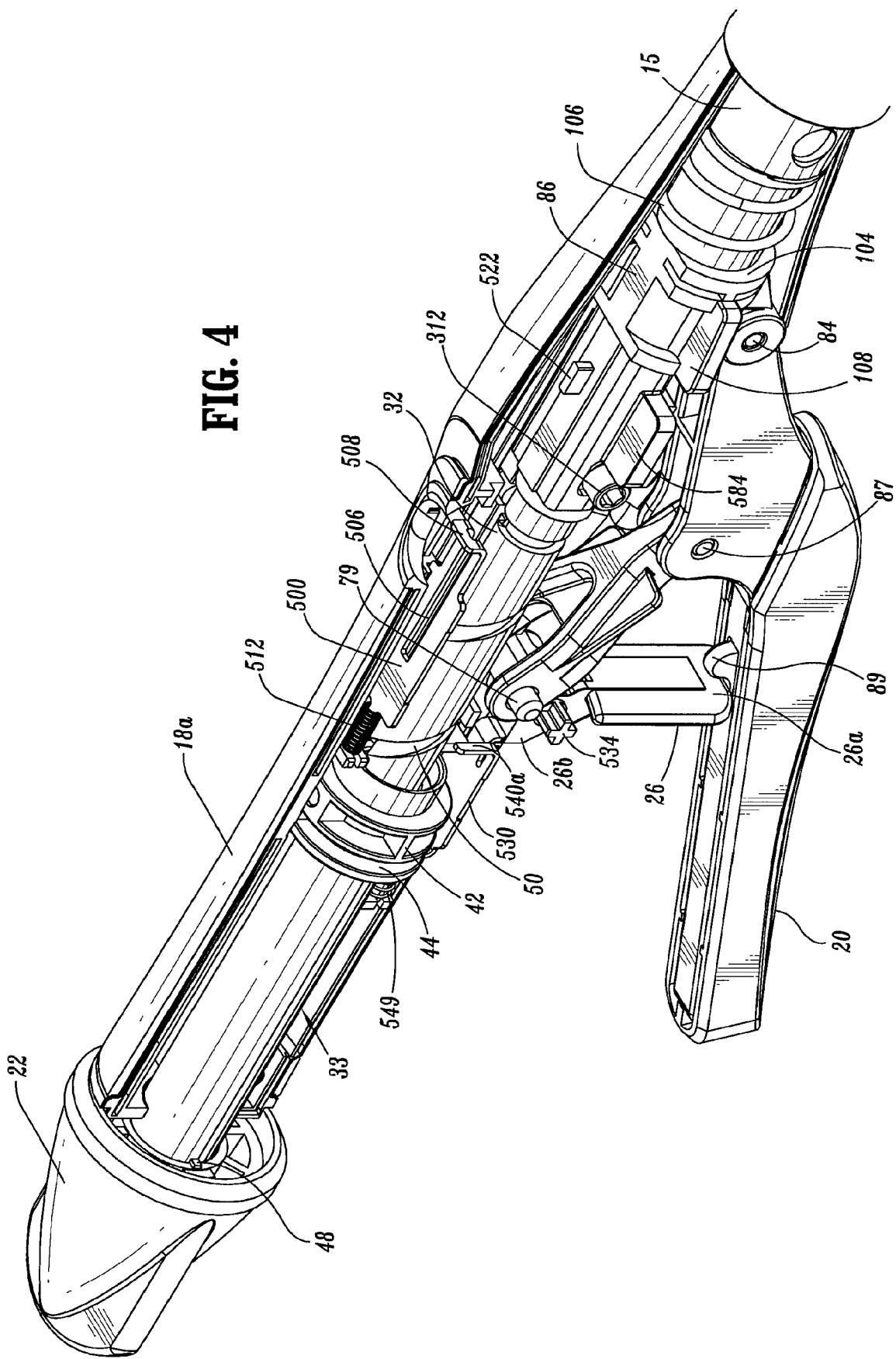

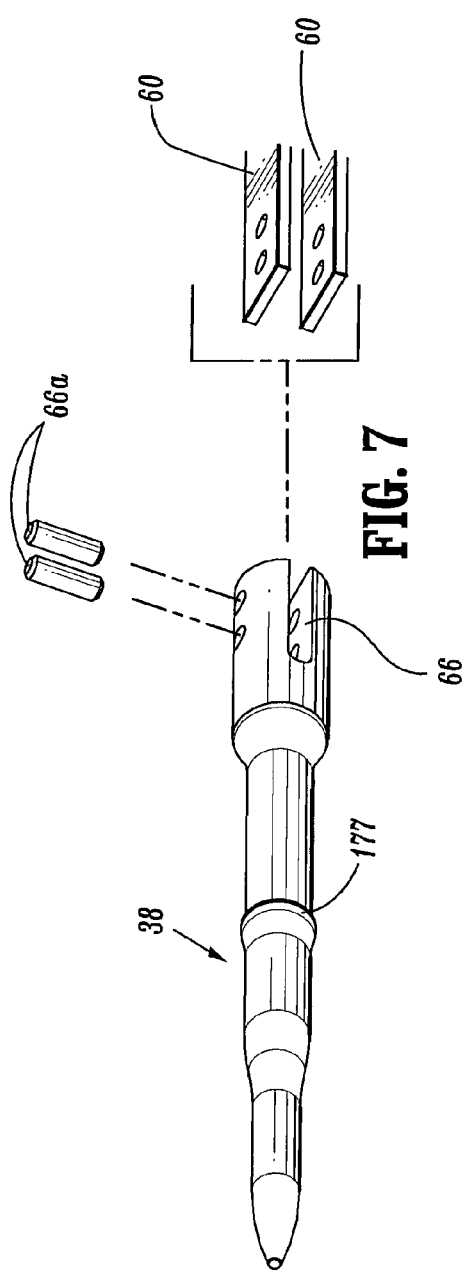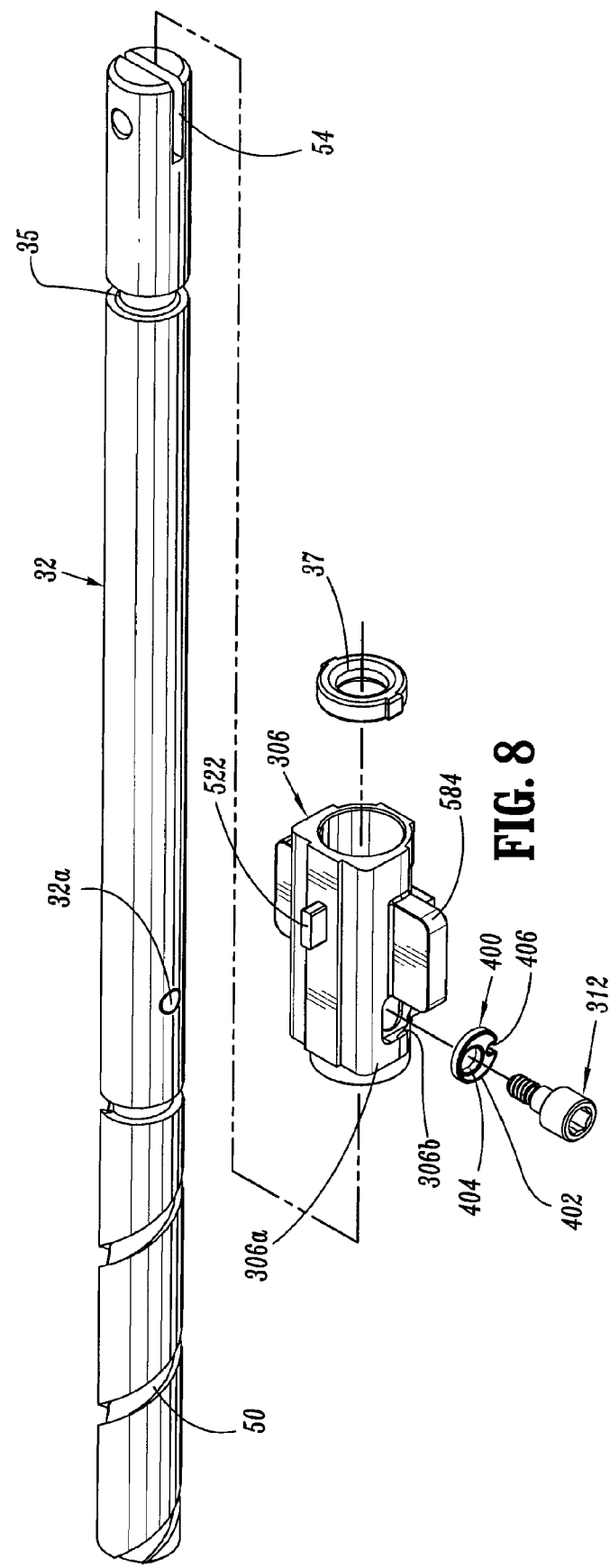

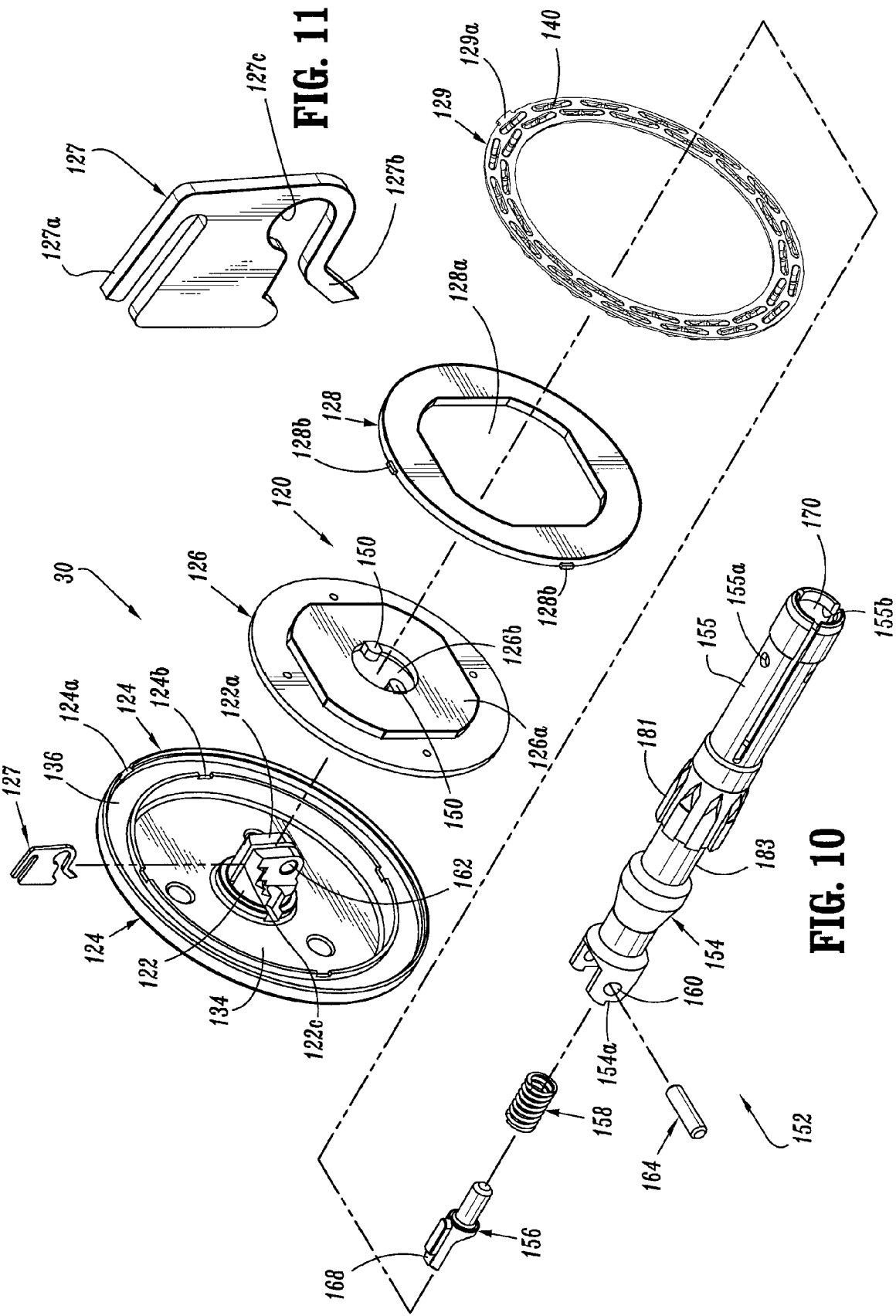

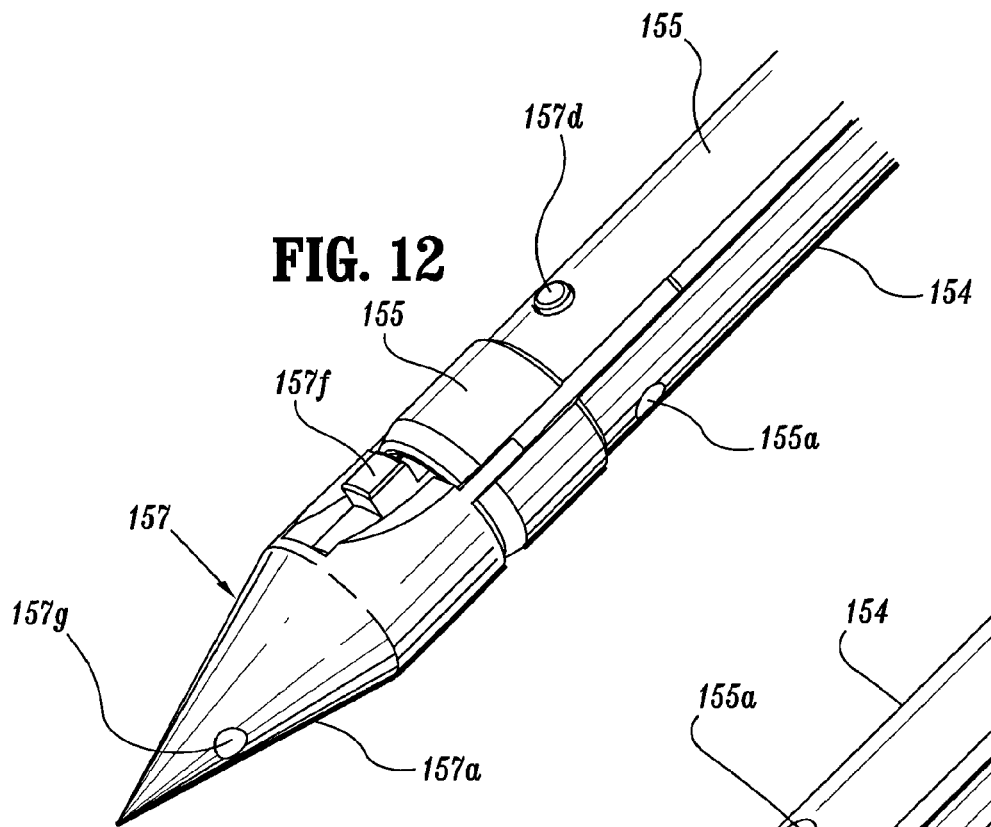
FIG. 12
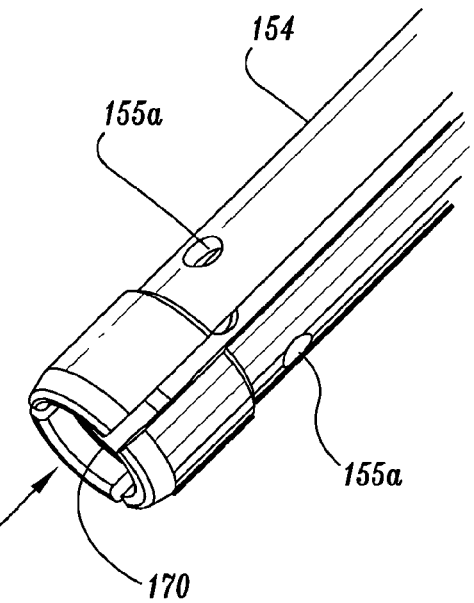
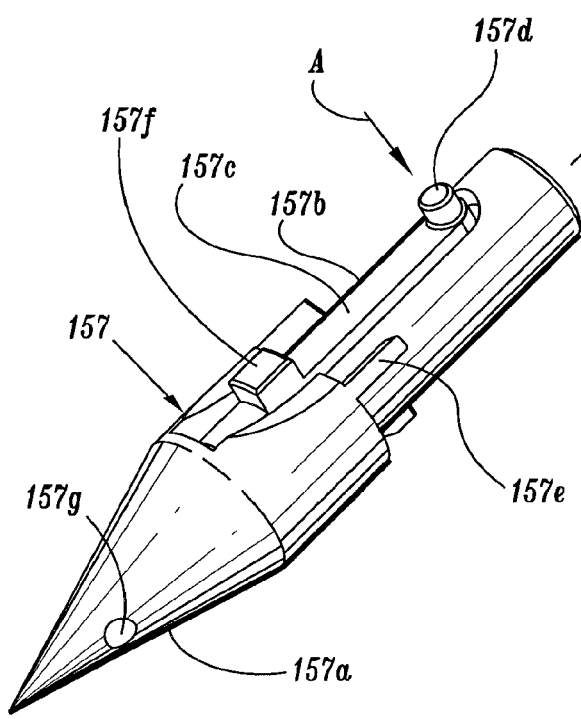
FIG. 13

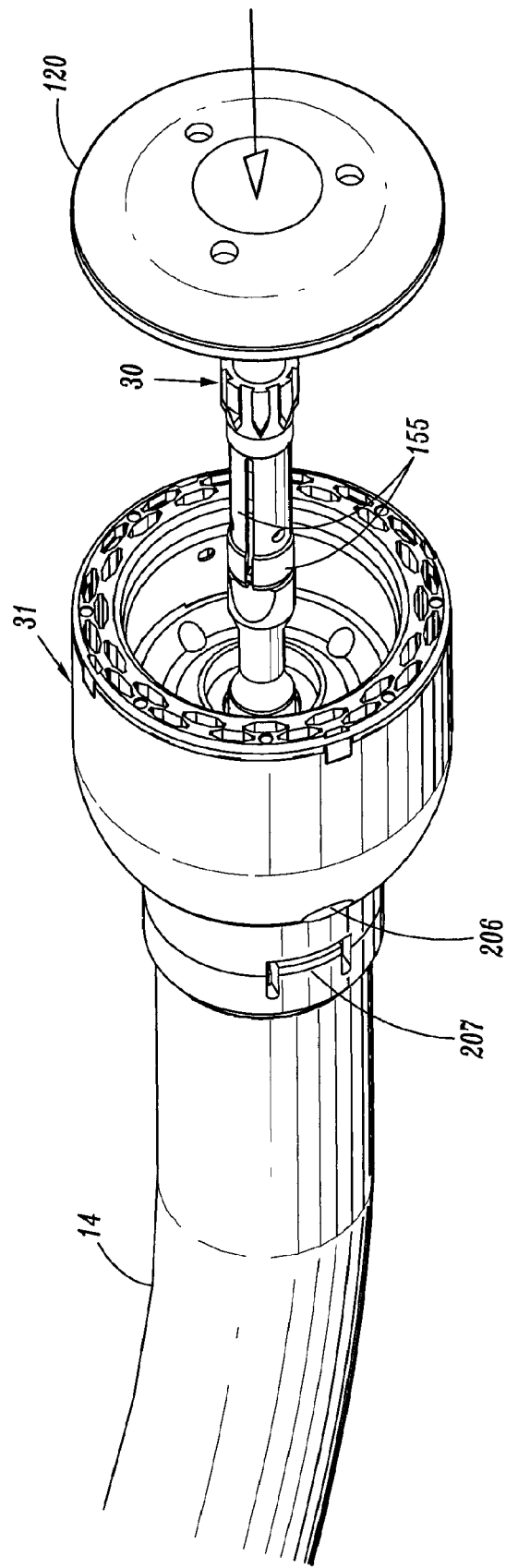
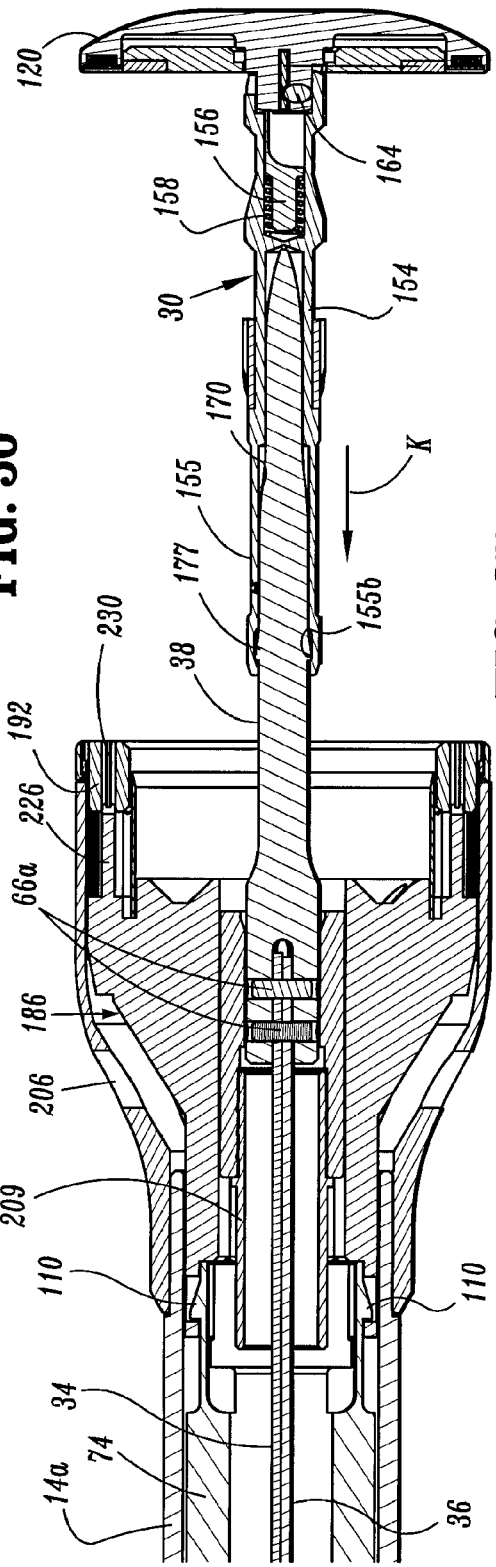
FIG. 36
FIG. 37

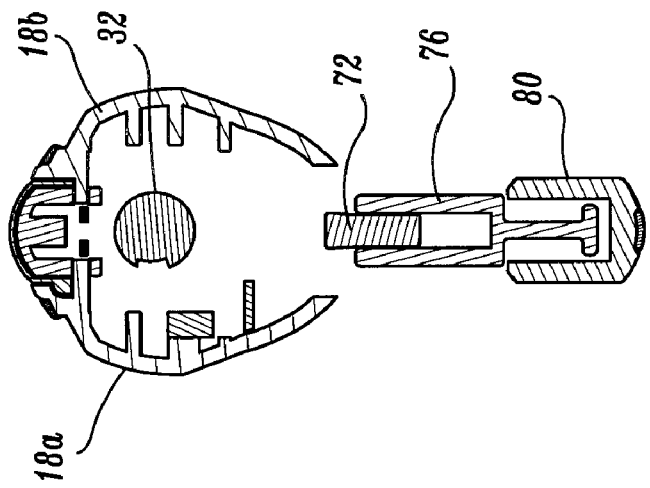
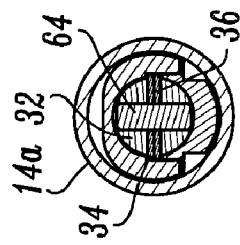
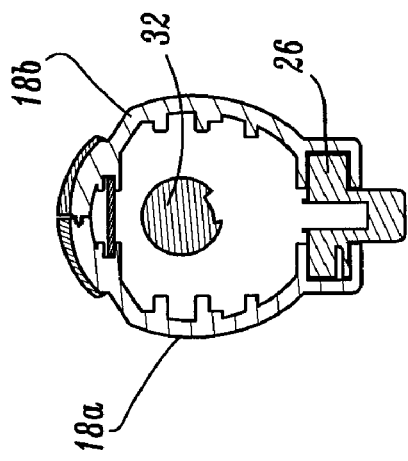
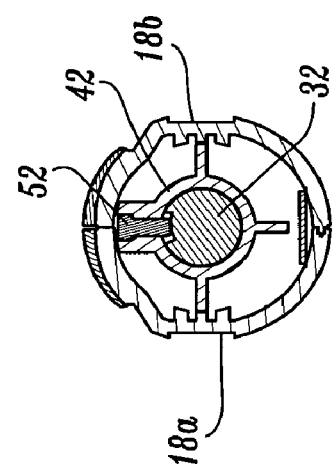
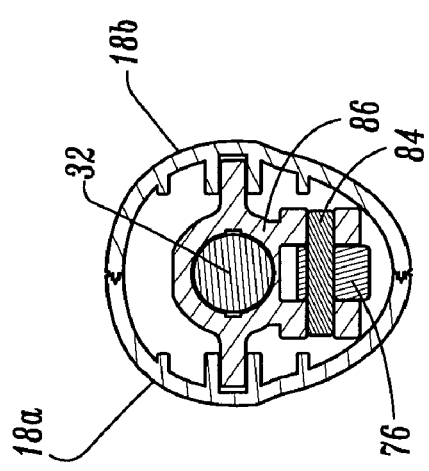
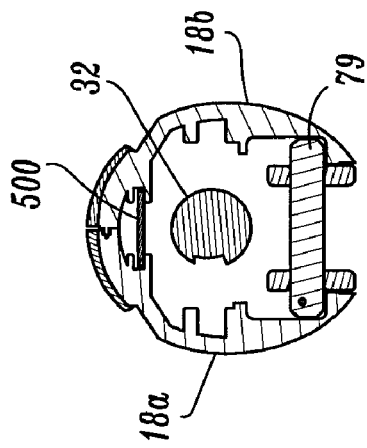

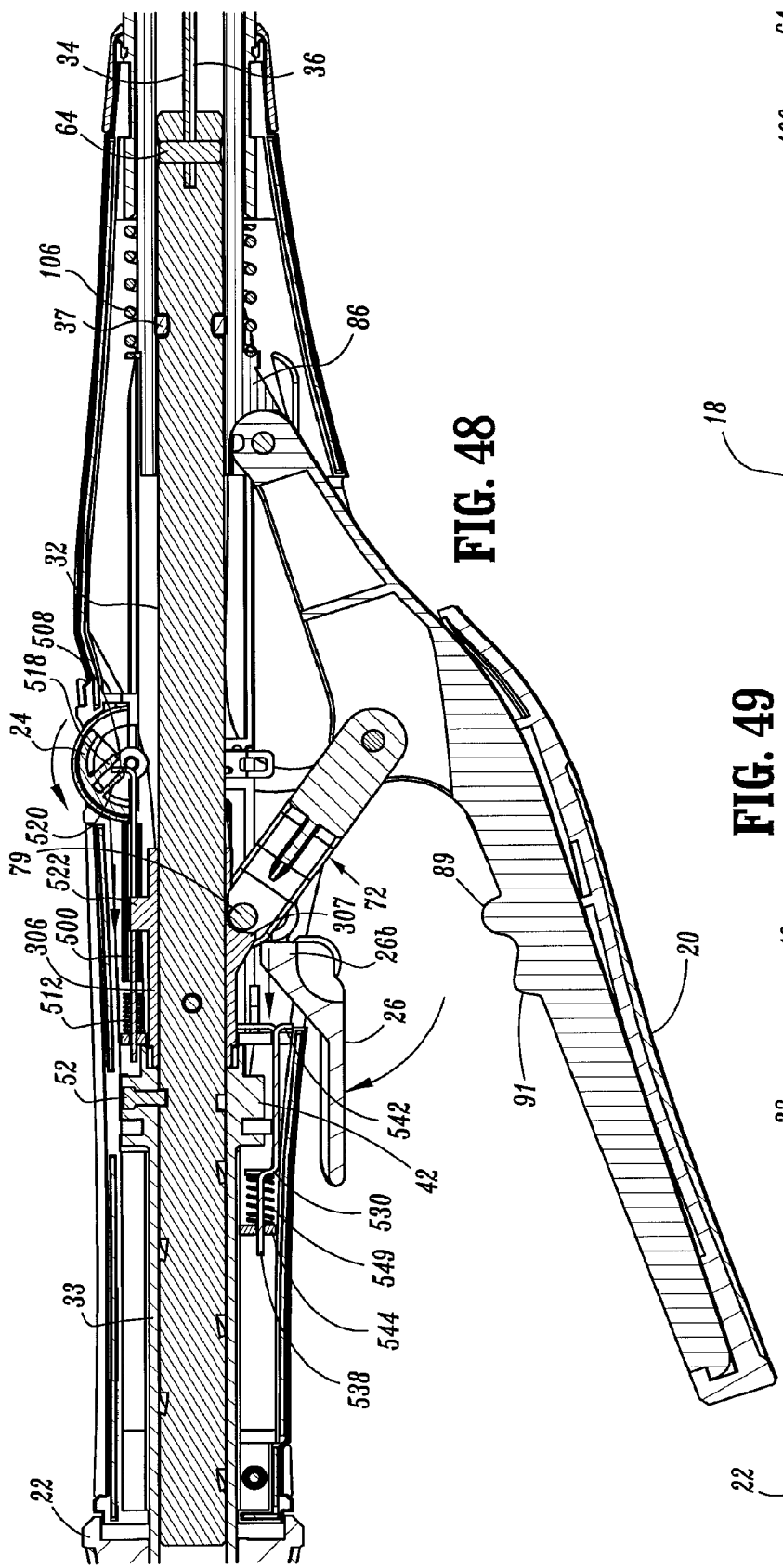
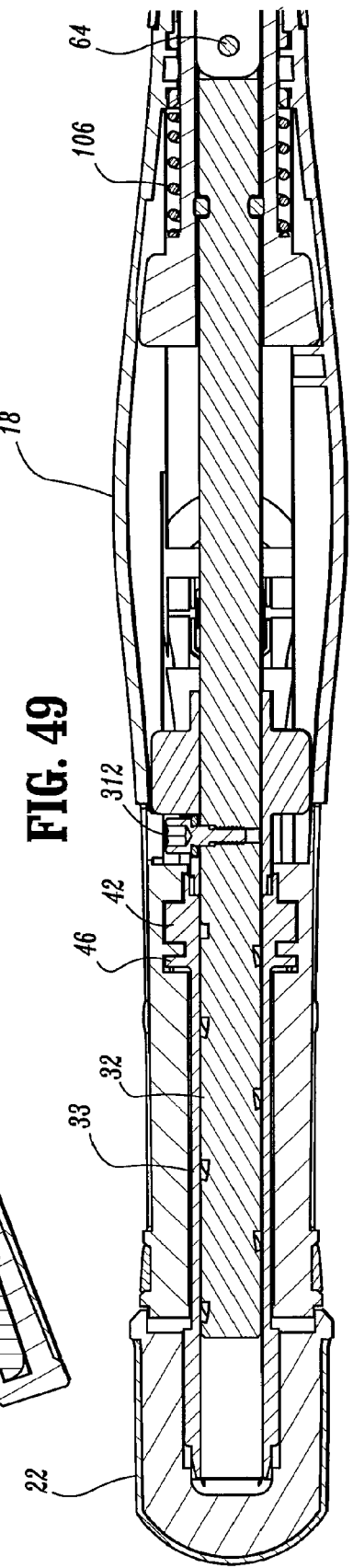
FIG. 48
FIG. 49

SURGICAL STAPLING DEVICE WITH COATED KNIFE BLADE

CROSS-REFERENCE TO RELATED APPLICATIONS

This application is a continuation of co-pending U.S. application Ser. No. 11/219,386, filed Sep. 2, 2005, and this application is also a continuation in part of co-pending U.S. application Ser. No. 11/158,860, filed Jun. 22, 2005, which in turn, is a continuation of U.S. application Ser. No. 09/964,901, filed Sep. 27, 2001, now U.S. Pat. No. 6,936,297. Each of the foregoing patent applications and patents are claimed as priority documents and the entire disclosures of each of which are incorporated by reference herein.

BACKGROUND

1. Technical Field

The present disclosure relates generally to a surgical stapling device for applying surgical staples to body tissue wherein the knife blade of the surgical stapling device is coated. More particularly, the present disclosure relates to a surgical stapling device suitable for performing circular anastomosis of hollow tissue organs wherein the knife blade of the surgical stapling device is coated with a lubricious coating.

2. Background to Related Art

Anastomosis is the surgical joining of separate hollow organ sections. Typically, an anastomosis procedure follows surgery in which a diseased or defective section of hollow tissue is removed and the remaining end sections are to be joined. Depending on the desired anastomosis procedure, the end sections may be joined by either circular, end-to-side or side-to-side organ reconstruction methods.

In a circular anastomosis procedure, the two ends of the organ sections are joined by means of a stapling instrument which drives a circular array of staples through the end section of each organ section and simultaneously cores any tissue interior of the driven circular array of staples to free the tubular passage. Examples of instruments for performing circular anastomosis of hollow organs are described in U.S. Pat. Nos. 6,053,390, 5,588,579, 5,119,983, 5,005,749, 4,646,745, 4,576,167, and 4,473,077, each of which is incorporated herein in its entirety by reference. Typically, these instruments include an elongated shaft having a handle portion at a proximal end to actuate the instrument and a staple holding component disposed at a distal end. An anvil assembly including an anvil rod with attached anvil head is mounted to the distal end adjacent the staple holding component. Opposed end portions of tissue of the organs to be stapled are clamped between the anvil head and the staple holding component. The clamped tissue is stapled by driving one or more staples from the staple holding component so that the ends of the staples pass through the tissue and are deformed by the anvil head. A circular knife blade is advanced into contact with the anvil to core any tissue positioned therebetween. Smooth movement of the knife blade through the tissue is desirable. It would also be desirable to avoid sticking of the tissue being cut or any portion of the anvil structure to the knife blade.

Accordingly, a need exists for a stapling device with a knife blade possessing enhanced lubricity for cutting tissue and minimizing sticking of the knife blade to tissue or other components of the stapling instrument.

SUMMARY

In accordance with the present disclosure, a surgical stapling device is disclosed preferably for performing circular anastomoses. The surgical stapling device includes a handle portion or assembly, a body portion and a head portion including an anvil assembly and a shell assembly and a knife blade possessing a lubricious coating which enhances the ability of the knife to cut through tissue and minimizes the knife sticking to tissue or other components of the surgical stapling device. The knife includes a tissue cutting end and a surface having a coating. Typically, the coating is on the tissue cutting end of the knife.

BRIEF DESCRIPTION OF THE DRAWINGS

Various preferred embodiments of the presently disclosed surgical stapling device are disclosed herein with reference to the drawings wherein:

FIG. 1 is a top side perspective view from the proximal end of the presently disclosed surgical stapling device in the unapproximated position;

FIG. 2 is a top side perspective view from the distal end of the surgical stapling device shown in FIG. 1;

FIG. 3 is a side perspective exploded view of the handle assembly of the surgical stapling device shown in FIG. 1;

FIG. 3A is a top perspective view of the indicator of the handle assembly shown in FIG. 3;

FIG. 4 is a side perspective view from the top of the handle assembly of the surgical stapling device shown in FIG. 1 with a handle section removed;

FIG. 7 is an enlarged side perspective of the anvil retainer and band portions of the central body portion shown in FIG. 6;

FIG. 8 is a side perspective view of the screw and screw stop of the approximation mechanism of the handle assembly shown in FIG. 5;

FIG. 10 is a side perspective exploded view from the proximal end of the anvil assembly of the surgical stapling device shown in FIG. 1;

FIG. 11 is a side perspective view of the retaining clip of the anvil assembly shown in FIG. 10;

FIG. 12 is a side perspective view of the distal end of the center rod of the anvil assembly shown in FIG. 10 with a removable trocar fastened thereto;

FIG. 13 is a side perspective view of the center rod and removable trocar shown in FIG. 11 separated one from the other;

FIG. 36 is a perspective view from the front of the distal end of the surgical stapling device shown in FIG. 35 with an anvil assembly attached thereto;

FIG. 37 is a side cross-sectional view of the distal end of the surgical stapling device shown in FIG. 36;

FIG. 39 is a cross-sectional view taken along section lines 39-39 of FIG. 38;

FIG. 40 is a cross-sectional view taken along section lines 40-40 of FIG. 38;

FIG. 41 is a cross-sectional view taken along section lines 41-41 of FIG. 38;

FIG. 42 is a cross-sectional view taken along section lines 42-42 of FIG. 38;

FIG. 43 is a cross-sectional view taken along section lines 43-43 of FIG. 38;

FIG. 44 is a cross-sectional view taken along section lines 44-44 of FIG. 38;

FIG. 48 is a side cross-sectional view of the handle assembly of the surgical stapling device shown in FIG. 45;

FIG. 49 is a top horizontal cross-sectional view of a portion of the handle assembly of the surgical stapling device shown in FIG. 45;

DETAILED DESCRIPTION OF PREFERRED EMBODIMENTS

Figure 5:
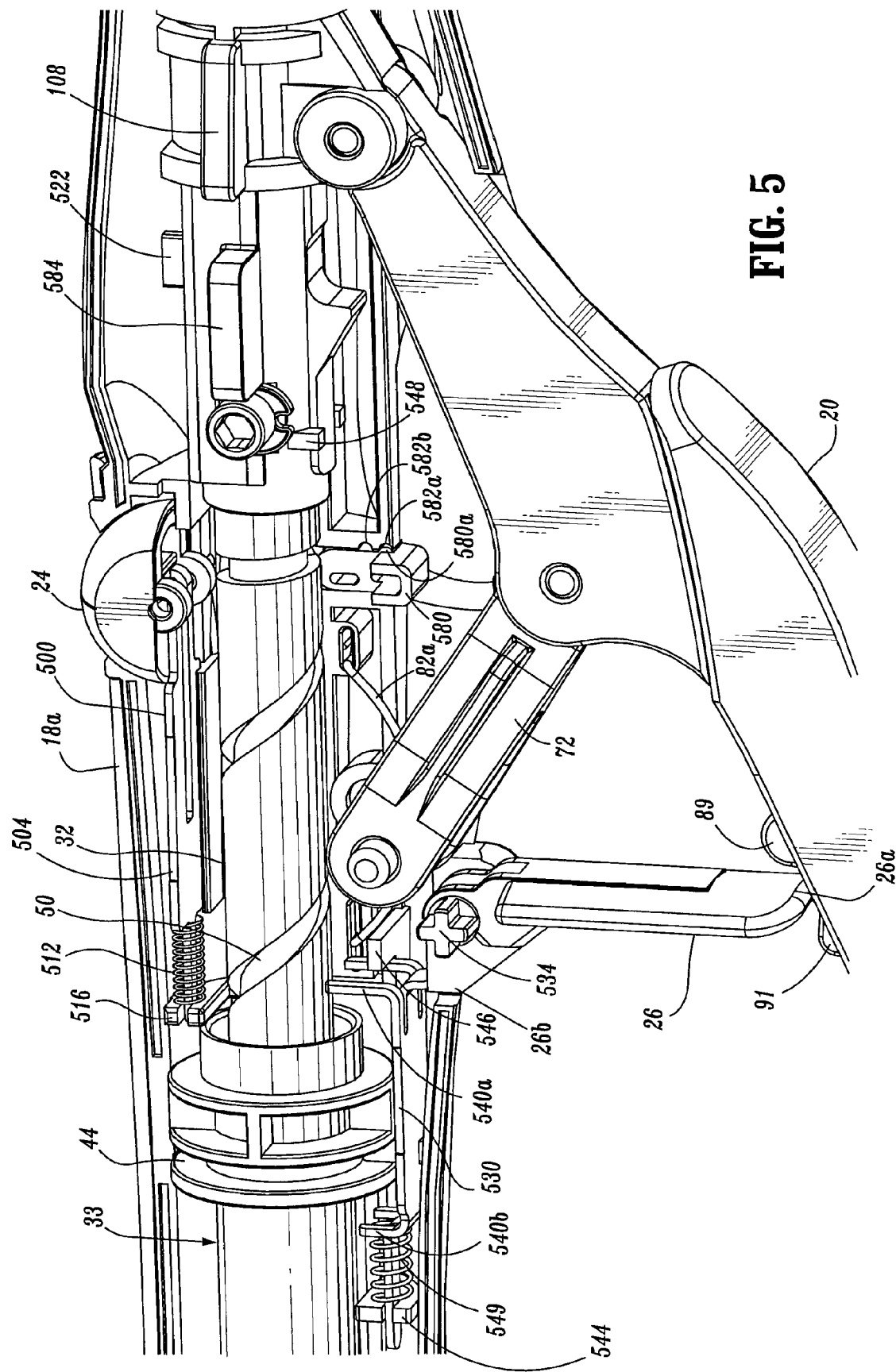
FIG. 5 is a side perspective view from the bottom of the handle assembly of the surgical stapling device shown in FIG. 4.

Preferred embodiments of the presently disclosed surgical stapling device will now be described in detail with reference to the drawings in which like reference numerals designate identical or corresponding elements in each of the several views.

Throughout this description, the term "proximal" will refer to the portion of the instrument closest to the operator and the term "distal" will refer to the portion of the instrument furthest from the operator.

FIGS. 1 and 2 illustrate one preferred embodiment of the presently disclosed surgical stapling device shown generally as 10. Briefly, surgical stapling device 10 includes a proximal handle assembly 12, an elongated central body portion 14 including a curved elongated outer tube 14a, and a distal head portion 16. Alternately, in some surgical procedures, e.g., the treatment of hemorrhoids, it is desirable to have a substantially straight, preferably shortened, central body portion. The length, shape and/or the diameter of body portion 14 and head portion 16 may also be varied to suit a particular surgical procedure.

Handle assembly 12 includes a stationary handle 18, a firing trigger 20, a rotatable approximation knob 22 and an indicator 24. Stationary handle 18 is preferably formed from thermoplastic handle sections 18a and 18b, e.g., polycarbonate, (FIG. 3) which together define a housing for the internal components of handle assembly 12. Handle sections 18a and 18b are preferably secured together by sonic welding. Alternately, other known securement techniques may be employed including screws, adhesives, snap-fit connectors, etc. The internal components of handle portion 12 will be discussed in detail below. Preferably, cushioned and/or resilient slip resistant portions such as a grip (not shown) can be fastened to or included as part of handle sections 18a and 18b and firing trigger 20. The slip resistant grip may be formed over handle sections 18a and 18b and firing trigger 20 using an overmolding procedure and may be formed from neoprene or rubber. Alternately, other suitable materials, e.g., elastomeric materials, and joining techniques may be employed. A pivotally mounted trigger lock 26 is fastened to handle assembly 12 and is manually positioned to prevent inadvertent firing of stapling device 10. Indicator 24 is positioned on the stationary handle 18 and includes indicia, e.g., color coding, alphanumeric labeling, etc., to identify to a surgeon whether the device is approximated and is ready to be fired. Indicator 24 preferably has a bulbous or convex shape which extends outwardly from a top surface of handle sections 18a and 18b and is easily viewable by a surgeon from the top and sides of the stapling device.

Head portion 16 includes an anvil assembly 30 and a shell assembly 31. Each of these assemblies will be discussed in detail below. Except where otherwise noted, the components of surgical device 10 are generally formed from thermoplastics including polycarbonates, and metals including stainless steel and aluminum. The particular material selected to form a particular component will depend upon the strength requirements of the particular component. For example, the anvil is preferably formed from a metal, such as stainless steel, and the stationary handle is preferably formed from a thermoplastic such as polycarbonate. Alternately, other materials not listed above, which preferably can withstand sterilization procedures, may be used to form components of stapling device 10 provided the materials are suitable for surgical use and meet the strength requirements of the particular component.

Figure 6:
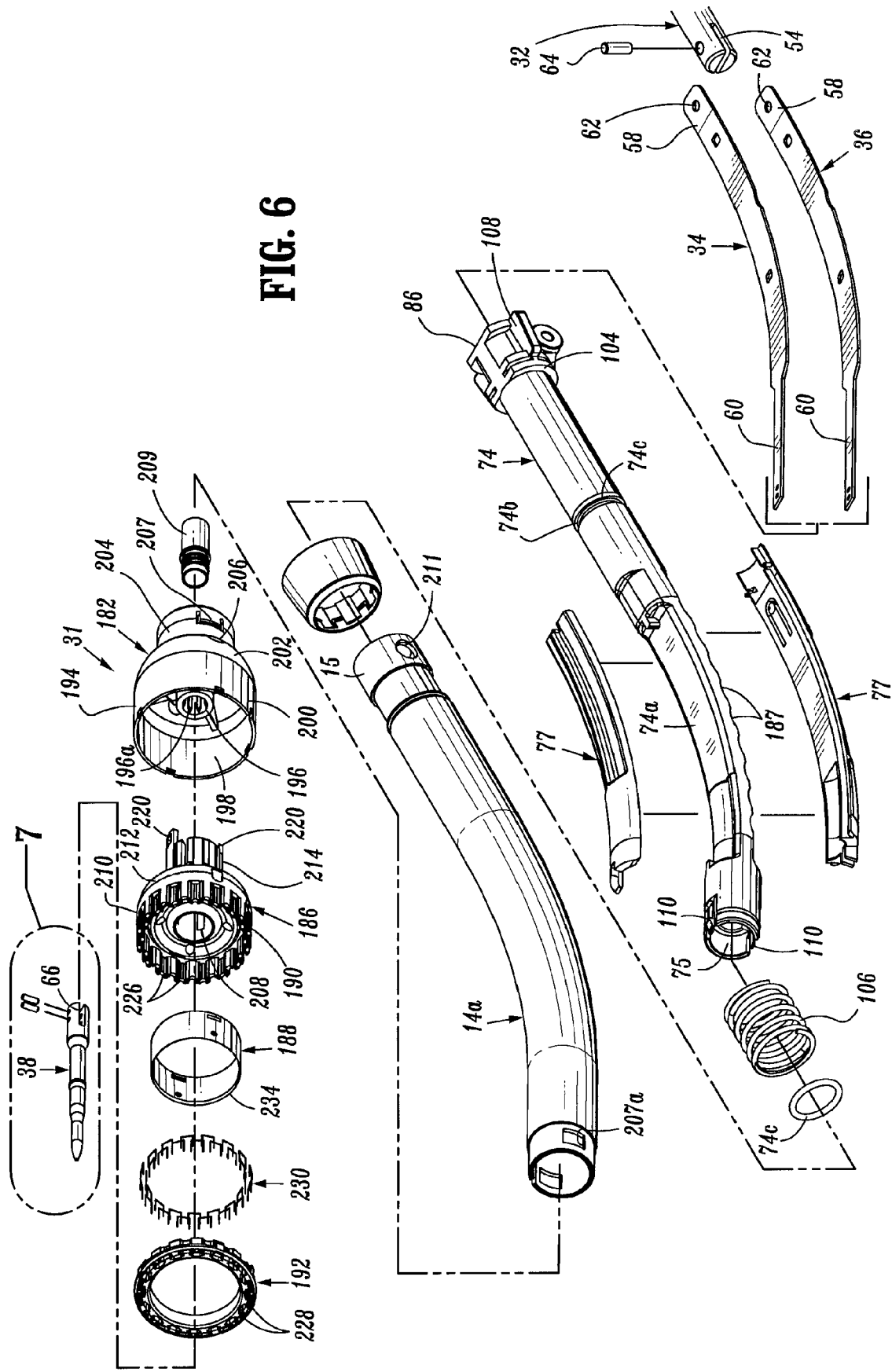
FIG. 6 is a side perspective exploded view of the central body portion and distal head portion of the surgical stapling device shown in FIG. 1.
Figure 9A:
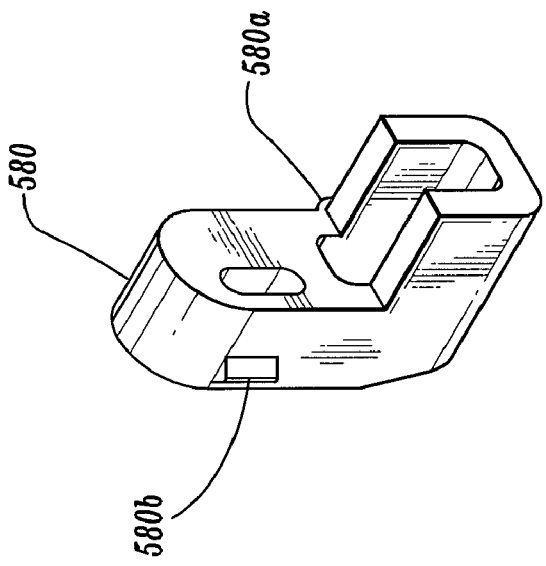
FIG. 9A is a side perspective view from the top of the abutment member of the handle assembly shown in FIG. 3.
Figure 9:
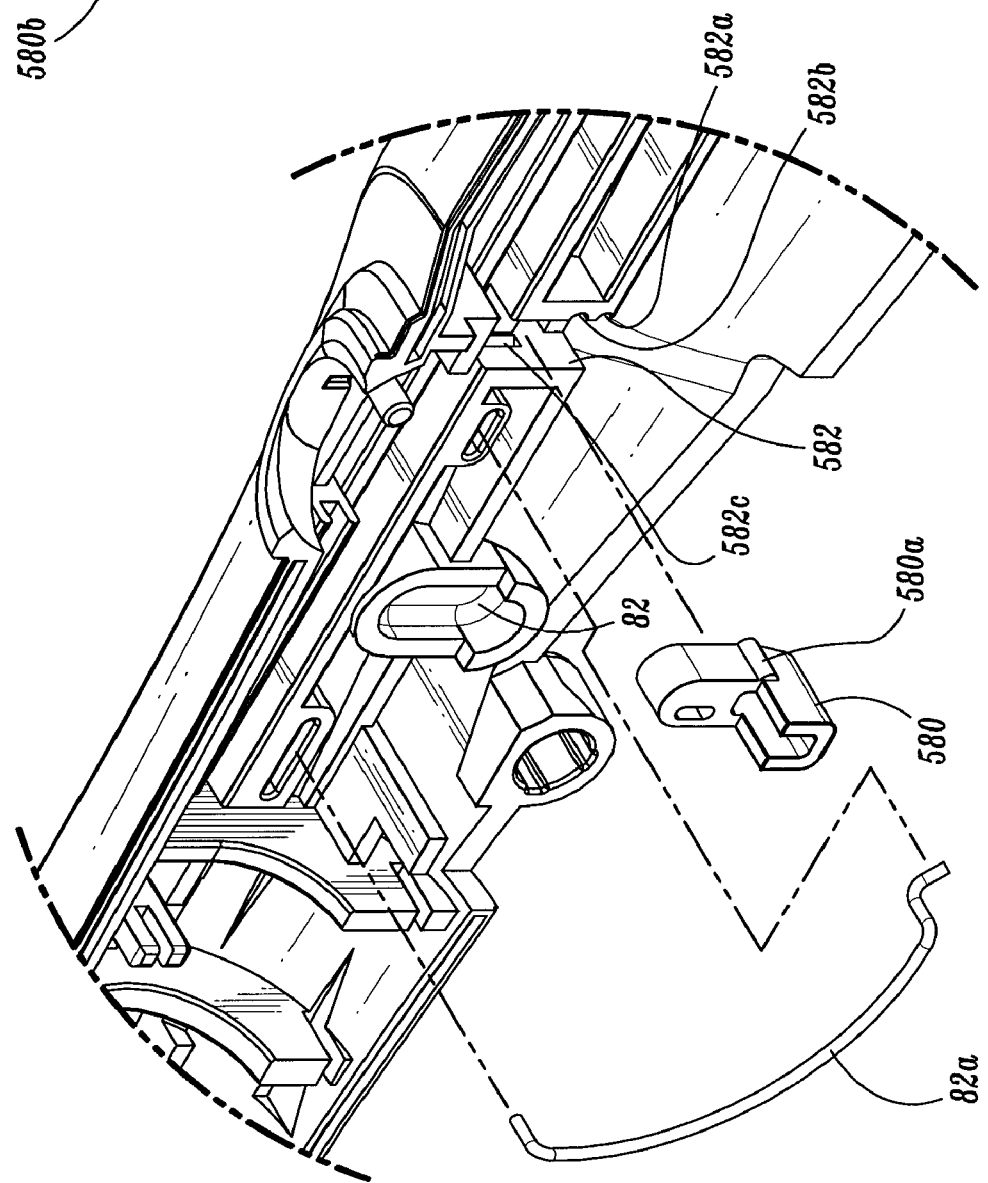
FIG. 9 is an enlarged view of the indicated area of detail shown in FIG. 3.

FIGS. 3-5 illustrate the internal components of handle assembly 12. The internal components include the proximal components of approximation and firing mechanisms, a firing lockout mechanism and an indicator drive mechanism. FIGS. 6 and 7 illustrate the internal components of elongated body portion 14. These components include the distal components of the approximation and firing mechanisms. Each of these mechanisms will be disclosed in detail hereinbelow.

Approximation Mechanism

Referring to FIGS. 3-8, the approximation mechanism includes approximation knob 22, a drive screw 32, a rotatable sleeve 33, first and second screw extensions 34 and 36 (FIG. 6), respectively, and an anvil retainer 38. Rotatable sleeve 33 includes a substantially cylindrical hollow body portion 40 and a substantially cylindrical collar 42 which together define a central bore 33a. Collar 42 has an annular groove 44 formed thereabout which is dimensioned to receive an inwardly extending flange 46 formed on an inner wall of handle sections 18a and 18b. Engagement between groove 44 and flanges 46 axially fixes sleeve 33 within handle 18 while permitting rotation of sleeve 33 in relation to stationary handle 18. The proximal end of body portion 40 of rotatable sleeve 33 extends through an opening 18b in the proximal end of stationary handle 18. A pair of diametrically opposed elongated ribs 48 are positioned or formed on the outer surface of body portion 40. Approximation knob 22 includes a pair of internal slots 49a positioned to receive ribs 48 of sleeve 33 to rotatably fix sleeve 33 to knob 22, such that rotation of knob 22 causes concurrent rotation of sleeve 33.

The proximal half of screw 32 includes a helical channel 50 and is dimensioned to be slidably positioned within central bore 33a of rotatable sleeve 33. The distal end of screw 32 includes an annular recess 35 dimensioned to receive a seal member 37 (FIG. 3) for providing a fluid tight seal between the outer surface of screw 32 and the inner surface of pusher link 74. A pin 52 (FIG. 3) extends radially through cylindrical collar 42 of sleeve 33 into helical channel 50. Since sleeve 33 is axially fixed with respect to stationary handle 18, rotation of sleeve 33 about screw 32 causes pin 52 to move along channel 50 of screw 32 to effect axial movement of screw 32 within stationary handle 18.

Referring to FIGS. 6-8, the distal end of screw 32 includes a transverse slot 54. Top and bottom screw extensions 34 and 36 (FIG. 6) each include a proximally located flexible flat band portion 58 and a distally located flat band portion 60. Alternately, it is envisioned that screw extensions 34 and 36 may have other than a band configuration. For example, screw extensions 34 and 36 may be semi-circular or circular in cross-section. The flexibility of top and bottom screw extensions 34 and 36 permits movement of screw extensions 34 and 36 through curved elongated body portion 14. The proximal end of each band portion 58 includes a hole 62 dimensioned to receive a pin 64 for securing the proximal end of screw extensions 34 and 36 within transverse slot 54 of screw 32. Alternately, other fastening techniques may be used to secure each band portion 58 to screw 32, e.g., welding, crimping, etc. Distally located band portion 60 of each screw extension 34 and 36 is dimensioned to be received within a transverse slot 66 formed in a proximal end of anvil retainer 38 (FIG. 7) to fasten anvil retainer 38 to the distal end of screw extensions 34 and 36. Preferably, a pair of pins 66a which extend through the proximal end of anvil retainer 38 and band portions 60 are used to secure screw extensions 34 and 36 to anvil retainer 38. Alternately, band portions 60 can be brazed or welded within slot 66 or other fastening techniques may be used to secure band portions 60 of screw extensions 34 and 36 to anvil retainer 38, e.g., screws, crimping, etc. Anvil retainer 38 includes an annular protrusion 177 (FIG. 7) which is configured to engage the anvil assembly in a manner to be discussed in detail below. Alternately, protrusion 177 need not be annular or may include different attachment structure, e.g., recesses, grooves, etc.

Referring again to FIGS. 3-7, when approximation knob 22 is manually rotated, rotatable sleeve 33 is rotated about the proximal end of screw 32 to move pin 52 along helical channel 50 of screw 32. Since sleeve 33 is axially fixed to stationary handle 18, as pin 52 is moved through channel 50, screw 32 is advanced or retracted within stationary handle 18. As a result, top and bottom screw extensions 34 and 36, which are fastened to the distal end of screw 32, and anvil retainer 38, which is fastened to the distal end of screw extensions 34 and 36, are moved axially within elongated body portion 14.

Since anvil assembly 30 is secured to the distal end of anvil retainer 38, rotation of approximation knob 22 will effect movement of anvil assembly 30 in relation to shell assembly 31 between spaced and approximated positions.

Firing Mechanism

Referring to FIGS. 3-6 and 9, the firing mechanism includes firing trigger 20, a firing link 72 and an elongated pusher link 74 (FIG. 6). Firing trigger 20 includes a body portion 76 and a trigger cover 80. A cushioned gripping surface (not shown) preferably formed of neoprene or rubber is provided on trigger cover 80. The cushioned gripping surface provides a non-slip cushioned surface to make actuation of device 10 more comfortable to a surgeon. The distal end of body portion 76 of trigger 20 is pivotally connected to a coupling member 86 by a pivot member 84. Coupling member 86 is secured to the proximal end of pusher link 74 and may be formed integrally with pusher link 74 or as a separate element fastened thereto. Firing link 72 has a distal end pivotally secured to body portion 76 of trigger 20 by a pivot member 87 and a second end pivotally secured within a vertical slot 82 formed between stationary handle half-sections 18a and 18b of stationary handle 18 by pivot member 79. Pivot member 79 is free to move vertically within slot 82. A spring 82a (FIG. 9) is supported within handle 18 to urge pivot member 79 downwardly towards the bottom of slot 82. Body portion 76 of trigger 20 further includes a pair of abutments including an abutment 89 and an abutment 91 which are positioned to engage the distal end 26a (FIG. 4) of trigger lock 26 in a manner to be described in greater detail below to prevent actuation of trigger 20 prior to approximation of device 10.

Coupling member 86 which is supported on the proximal end of elongated pusher link 74 includes a flange 104 (FIG. 6). A spring 106 is positioned between a proximal end 15 of outer tube 14a and flange 104 (FIG. 4) to bias pusher link 74 proximally to a retracted, non-fired position. A pair of wings 108 extend radially outwardly from coupling member 86. Wings 108 are dimensioned to slide along channels 111 (FIG. 3) formed along the internal walls of stationary handle 18 to maintain proper alignment of pusher link 74 within stationary handle 18 during firing of device 10.

Referring to FIG. 6, the distal end of pusher link 74 includes a pair of engagement fingers 110 which are dimensioned to lockingly engage with members 220 formed in the proximal end of pusher back 186. Pusher back 186 forms part of shell assembly 31 and will be discussed in greater detail below. Pusher link 74 is preferably formed from a flexible plastic material and includes a plurality of notches 187 which allow the pusher link to bend more easily as it moves through body 14. Pusher link 74 defines a hollow channel 75 for slidably receiving the approximation mechanism. A flat surface or cutout 74a (FIG. 6) formed in pusher link 74 slidably supports screw extensions 34 and 36 which are positioned in juxtaposed alignment. Spacers 77 are positioned within outer tube 14a adjacent cutout 74a to provide additional support for screw extensions 34 and 36 and pusher link 74 to prevent each component from buckling during actuation. An annular channel 74b is formed about pusher link 74 to receive an O-ring seal 74c. Pusher link 74 is slidably positioned within body portion 14 such that O-ring 74c seals the space between pusher link 74 and an internal wall of outer tube 14a. Operation of the firing mechanism of the device will be described in detail below.

Referring again to FIGS. 3-6 and 9, when firing trigger 20 is actuated, i.e., pivoted about pivot member 84, firing link 72 is moved proximally until pivot member 79 engages an abutment surface 307 (FIG. 25A-D) formed on screw stop 306 (FIG. 3). Screw stop 306 is axially fixed to screw 32 in a manner to be described in detail below. Thereafter, firing trigger 20 is pushed distally to advance pusher link 74 distally against the bias of spring 106. Since the distal end of pusher link 74 is connected to pusher back 186, actuation of firing trigger 20 effects advancement of pusher back 186 within shell assembly 31 to eject staples from shell assembly 31 in a manner to be described below.

Anvil Assembly

Referring to FIGS. 10-21, anvil assembly 30 includes an anvil head assembly 120 and an anvil center rod assembly 152. Anvil head assembly 120 includes a post 122, an anvil head 124, a backup plate 126, a cutting ring 128, a retaining clip 127 and an anvil 129. Post 122 is centrally positioned through a bore in anvil head 124. Alternately, post 122 may be integrally formed with anvil head 124. Anvil 129 is supported on anvil head 124 in an outer annular recess 136 and includes a plurality of pockets 140 for receiving and deforming staples. At least one tab 129a extends radially outwardly from anvil 129 and is dimensioned to be received within a cutout 124a formed in anvil head 124. Tab 129a and cutout 124a function to align anvil 129 within annular recess 136. Backup plate 126 includes a central opening 126b which is positioned about post 122 within an inner recess 134 of anvil head 124 between post 122 and annular recess 136. Backup plate 126 includes a raised platform 126a. Cutting ring 128 includes an opening 128a having a configuration substantially the same as platform 126a. Opening 128a is positioned about platform 126a to rotatably fix cutting ring 128a on backup ring 126. Preferably, cutting ring 128 is formed from polyethylene and is fixedly secured to backup plate 126 using, for example, an adhesive. Backup ring 126 is preferably formed from metal and provides support to cutting ring 128 to enhance the cutting of tissue. Alternately other materials of construction may be used to construct plate 126 and ring 128. Cutting ring 128 and backup plate 126 are slidably mounted about post 122. Backup plate 126 includes a pair of inwardly extending tabs 150 which will be described in further detail below. Cutting ring 128 includes tabs 128b which are received within cutouts 124b formed in anvil head 124 to properly align backup ring 126 and cutting ring 128 within anvil head 124.

Anvil center rod assembly 152 includes anvil center rod 154, a plunger 156 and plunger spring 158. A first end of center rod 154 includes a transverse throughbore 160 which is offset from the central longitudinal axis of center rod 154. Post 122 of anvil head assembly 120 also includes a transverse throughbore 162. A pivot member 164 pivotally secures post 122 to center rod 154 such that anvil head assembly 120 is pivotally mounted to anvil center rod assembly 152. Plunger 156 is slidably positioned in a bore 154b (FIG. 16) formed in the first end of center rod 154. Plunger 156 includes an engagement finger 168 which is offset from the pivot axis of anvil head assembly 120 and biased into engagement with the base 122a of post 122 by plunger spring 158 to urge anvil head assembly 120 to a pivoted position at an angle to center rod 154. In a prefired untilted position, tabs 150 formed on backup plate 126 engage a top surface 154a (FIG. 20) of center rod 154 to prevent anvil head assembly 120 from pivoting about pivot member 164. As device 10 is fired, backup plate 126 and cutting ring 128 are moved deeper into anvil recess 134 of anvil head 124 about post 122 (FIG. 21) by knife 188 (FIG. 6) in a manner to be described in further detail below to move tabs 150 out of engagement with top surface 154a of center rod 154 to permit plunger 156 to pivot anvil head assembly 120 about pivot member 164.

Figure 17:
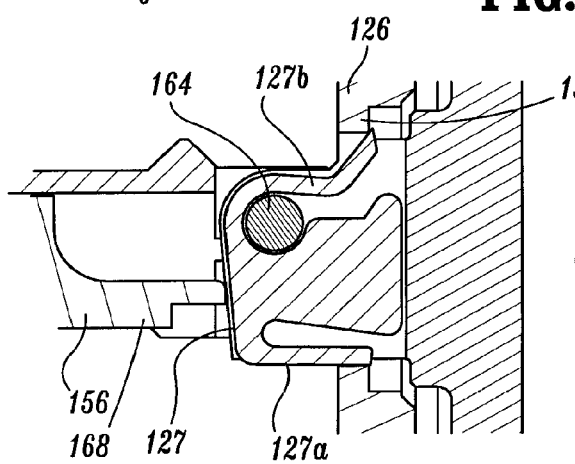
FIG. 17 is an enlarged view of the indicated area of detail shown in FIG. 16.
Figure 18:
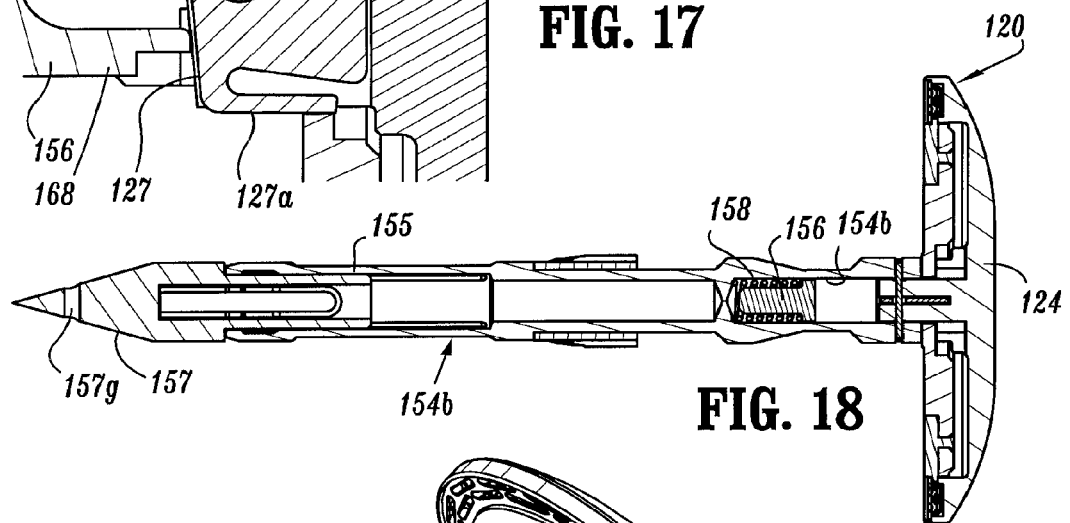
FIG. 18 is a side cross-sectional view taken through the pivot member of the anvil head assembly of the anvil assembly shown in FIG. 15.
Figure 19:
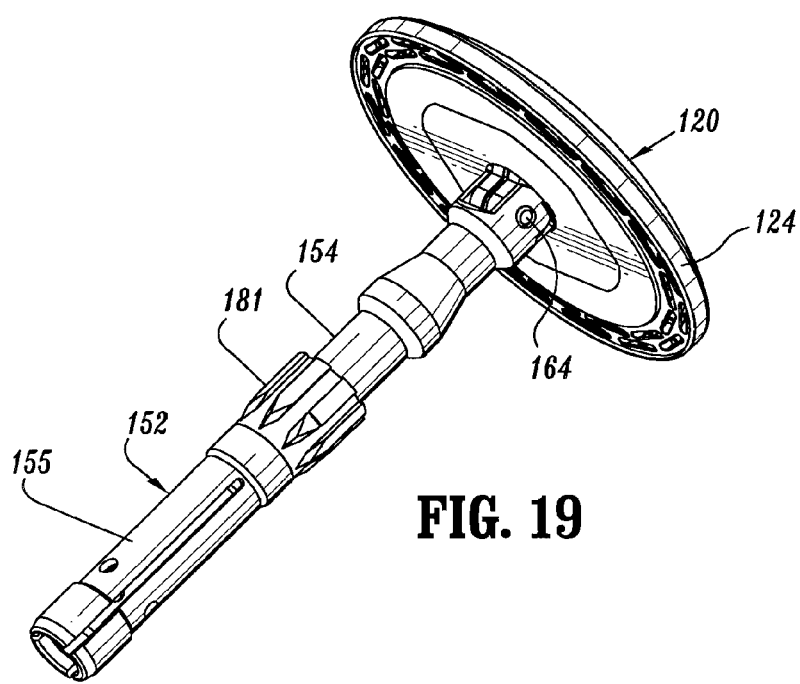
FIG. 19 is a side perspective view from the proximal end of the anvil assembly shown in FIG. 18 with the removable trocar removed.
Figure 21:
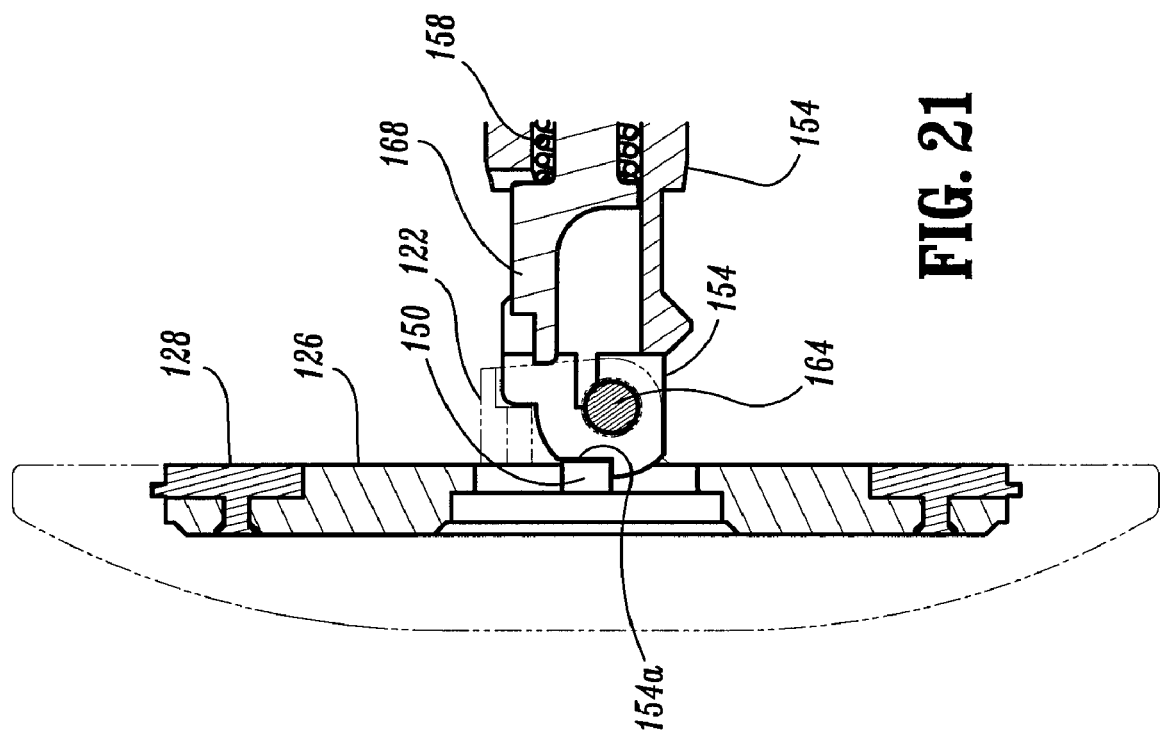
FIG. 21 is a side cross-sectional partial cutaway view of the distal portion of the anvil assembly shown in FIG. 19, with the anvil head in phantom.
Figure 20:
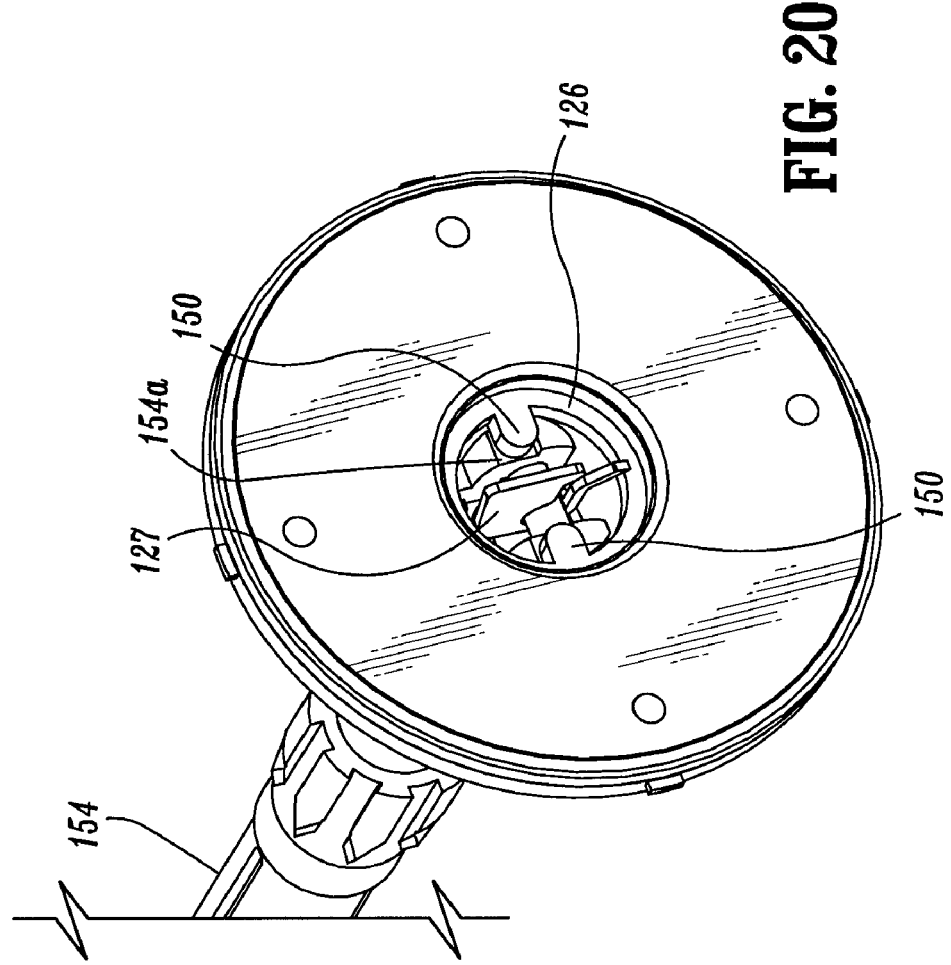
FIG. 20 is a perspective, partial cutaway view from the distal end of the anvil assembly shown in FIG. 19, with the anvil head removed.
Figure 22:
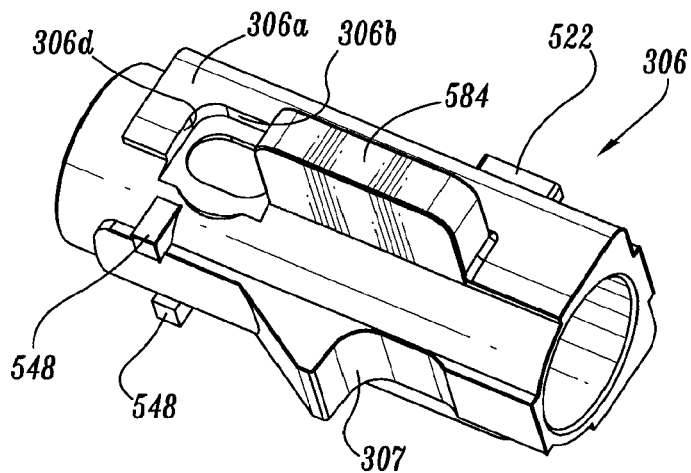
FIG. 22 is a side perspective view from the bottom of the screw stop of the handle assembly shown in FIG. 3.

A retainer clip 127 is positioned in a transverse slot 122c formed in post 122 and includes a pair of outwardly biased flexible arms 127a and 127b. Arm 127b includes a recess 127c dimensioned to receive pivot pin 164 (FIG. 17). Prior to firing device 10, arms 127a and 127b are deformed inwardly by backup plate 126 (FIG. 17). After device 10 has been fired and backup plate 126 has been pushed deeper into anvil head 124 by knife 188, flexible arms 127a and 127b spring outwardly to a position in front of backup plate 126. In this position, arms 127a and 127b prevent cutting ring 128 and backup plate 126 from sticking to the knife when anvil assembly 30 is unapproximated. It is envisioned that a retainer clip may be used in conjunction with non-pivotal anvil assemblies wherein the anvil head post and the anvil center rod are integrally formed.

In embodiments, knife 188 may be coated with a material to enhance its lubricity. Such a coating may allow knife 188 to more easily pass through tissue and prevent knife 188 from sticking to materials with which knife 188 comes into contact, such as tissue and cutting ring 128.

In embodiments, knife 188 may be coated with a coating mixture containing at least one polydialkylsiloxane having a molecular weight sufficient to provide a viscosity of the coating mixture of at least about 10,000 cp and at least one siliconization material.

Suitable polydialkylsiloxanes for use in forming the coating mixture herein include polydimethylsiloxanes, polydiethylsiloxanes, polydipropylsiloxanes, polydibutylsiloxanes and the like with polydimethylsiloxanes being preferred. Particularly preferred polydimethylsiloxanes are polydimethylsiloxanes having a molecular weight sufficient to provide a viscosity of the coating mixture of at least about 10,000 cp and preferably of at least about 30,000 cp. Such polydimethylsiloxanes for use herein include products sold by Dow Corning under the name "SYL-OFF® DC 23", which is suitable as a high density condensable polydimethylsiloxane, and NuSil Technology under the name "MED-4162" (30,000 cp.)

Suitable siliconization materials for addition with the foregoing polydialkylsiloxanes to form the coating mixtures of this disclosure include siliconization materials containing an aminoalkyl siloxane and at least one other copolymerizable siloxane, e.g., an alkylpolysiloxane or a cyclosiloxane; a silicone oil, e.g., one sold by Dow Corning Corporation under the name Dow 360 MEDICAL FLUID (350 to 12,500 centistokes), and the like, with a siliconization material containing an aminoalkyl siloxane and at least one other copolymerizable siloxane being useful in some embodiments. Typically, the siliconization material includes (a) from about 5 to about 70 weight percent of an aminoalkyl siloxane of the general formula:

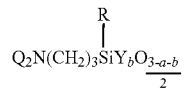

wherein R is a lower alkyl radical containing no more than about 6 carbon atoms; Y is selected from the group consisting of —OH and —OR' radicals in which R' is an alkyl radical of no more than about 3 carbon atoms; Q is selected from the group consisting of hydrogen, —CH$_3$ and —CH$_2$CH$_2$NH$_2$; a has a value of 0 or 1, b has a value of 0 or 1 and the sum of a+b has a value of 0, 1 or 2; and (b) from about 30 to about 95 weight percent of a methyl substituted siloxane of the general formula:

wherein R" is selected from the group consisting of —OH and —CR$_3$ radicals and c has a value of 1 or 2. In some embodiments, the two components of this siliconization material copolymerize, forming a lubricating coating on the surface of the blade.

In addition to, or in lieu of, the foregoing second copolymerizable siloxane, one can use one or more cyclosiloxanes such as, e.g., those described in the "Encyclopedia of Polymer Science and Engineering", Mark et al., eds., 2$^{nd}$ ed., Vol. 15, John Wiley & Son (1989), p. 207 et seq., the contents of which are incorporated by reference herein.

In some embodiments, a siliconization material for use herein in combination with the aforementioned polydimethylsiloxane(s) to form the coating mixture is Dow Corning Corporation's Dow Corning® MDX 4-4159 Fluid ("MDX Fluid"), an active solution of dimethyl cyclosiloxanes and dimethoxysilyidimethylaminoethylaminopropyl silicone polymer in a mixture of Stoddard solvent (mineral spirits) and isopropyl alcohol. Another suitable siliconization material for use herein is MED-4159 which is available from NuSil Technology LLC, Carpinteria, Calif.

The coating can be applied to knife 188 as a composition that further includes a solvent. Suitable solvents will be readily apparent to those skilled in the art once the siliconization material is chosen. Suitable solvents include, for example, hydrocarbon solvents having from about 5 to about 10 carbon atoms (e.g., pentane, hexane, heptane, octane, and the like), xylene, chlorinated solvents, THF, dioxanone, hydrofluoroethers and the like, and combinations thereof. Suitable hydrofluoroethers include, for example, HFE-71DE, HFE-72DE, HFE-71DA, HFE-71IPA, HFE-7100, and HFE-7200, available from 3M Chemicals (St. Paul, Minn.), combinations thereof, and combinations thereof with other solvents, such as those noted above.

In one embodiment of the present disclosure, a coating mixture can be formed by adding a first solution of at least one of the foregoing polydialkylsiloxanes in a solvent with a second solution of at least one of the foregoing siliconization materials in a solvent. The first solution is typically formed from SYL-OFF DC 23 or MED-4162 with a solvent such as hexane, HFE-71 DE, or HFE-72DE, with SYL-OFF DC 23 or MED-4162 being present in a concentration of from about 10 g/l to about 70 g/l, in embodiments from about 35 g/l to about 45 g/l. The second solution may be prepared in the form of a dilute organic solution, e.g., MDX Fluid (or other siliconization material) combined with a solvent so that the MDX Fluid is present at a concentration of from about 10 g/l to about 80 g/l and in embodiments from about 20 g/l to about 40 g/l. In some useful embodiments, the siliconization material is a mixture of MED-4162 and MDX Fluid.

The mixture may be formed by adding the first solution of the polydialkylsiloxane in solvent with the second solution of the siliconization material in solvent at a ratio of first solution to second solution from about 12:1 to about 1:12, in embodiments from about 6:1 to about 1:6, typically from about 2:1 to about 1:2. As one skilled in the art will readily appreciate, the amount of the first and second solutions necessary in forming the mixtures herein will vary depending on the volume of mixture desired.

Once the coating mixture is formed, it can then be applied to the foregoing knives employing techniques within the purview of one skilled in the art, e.g., by dipping, wiping, spraying, total immersion, etc. Typically, the coating is applied to at least the tissue cutting end of the knife. In some embodiments, dipping and spraying may be useful for applying the coating mixture of the present disclosure. Typically, knife 188 may be dipped into the coating mixture for about 5 to about 60 seconds, in embodiments from about 10 to about 45 seconds, typically from about 15 to about 30 seconds, to form a coating on the knife blades. After evaporation of any dilutant or solvent carrier, the siliconized coating may be cured to the desired degree.

The coating can be cured by, for example, first placing the coated knife blade in a humid environment, e.g., a humidification chamber, and exposing the coated knife blade to a temperature of from about 10° C. to about 50° C., in embodiments from about 20° C. to about 35° C., in a relative humidity of from about 20% to about 80%, in embodiments from about 50% to about 65%. The coated knife blades may be subjected to the foregoing temperatures and humidities to initiate curing to the desired degree and provide an improved lubrication coating. Typically, a time period ranging from about 1 hour to about 6 hours, in embodiments from about 2 hours to about 4 hours may be employed. The coated knives are then placed in, e.g., a furnace or oven, and cured by heating the knife blades to a temperature of from about 100° C. to about 200° C., in embodiments from about 110° C. to about 150° C., typically from about 115° C. to about 150° C., for a time period ranging from about 2 hours to about 48 hours, typically from about 15 hours to about 25 hours, such that cross-linking of the polydialkylsiloxane and siliconization material occurs. In a particularly useful embodiment, the coated knife blades may be heated to a temperature of about 140° C. for about 4 hours and a temperature of about 120° C. for about 20 hours.

In other embodiments, a coating may be applied to a knife by spraying. In this embodiment, a coating solution may be prepared as follows. A coating solution may be prepared by combining MED-4162 with MDX4-4159 in a suitable solvent. The ratio of MED-4162 to MDX4-4159 in the coating solution may be from about 5:0.25, typically from about 2.5:0.5, more typically from about 2:0.75.

In applying the coating solution by spraying, the knife blades may be placed on a tray with a tissue cutting end of the knife blade in the air and the second end of the knife blade in contact with the tray. The desired coating composition may then be applied using a spray gun or similar device. The coated blades may then be placed in a convection oven and cured at about 100° C. to about 200° C., in embodiments from about 120° C. to about 180° C., in embodiments from about 145° C. to about 175° C. for a period of time from about 1 hour to about 5 hours, in embodiments from about 1.5 hours to about 4 hours, in embodiments from about 2 hours to about 3 hours. This heating step evaporates the solvents, leaving a silicone coating on the blade of the MED-4162 and MDX4-4159 at a ratio of from about 5:0.25, typically from about 2.5:0.5, more typically from about 2:0.75.

A second end of center rod 154 includes a bore 170 defined by a plurality of flexible arms 155*a*. Bore 170 is dimensioned to receive a removable trocar 157. At least one of flexible arms 155, and preferably a plurality of flexible arms 155, e.g., three, include an opening 155*a* dimensioned to receive a projection 157*d* formed on removable trocar 157 to releasably secure trocar 157 to center rod 154 (FIG. 13). The distal ends of each of flexible arms 155 include an internal shoulder 155*b* (FIG. 10) dimensioned to releasably engage anvil retainer 38 in a manner to be discussed in detail below. A plurality of splines 181 are formed about center rod 154 and are dimensioned to be received within grooves 196*a* (FIG. 6) in shell assembly 31 to align anvil assembly 30 within shell assembly 31 during approximation of the anvil and shell assemblies. Center rod 154 also includes an annular recessed portion 183 to facilitate grasping of anvil assembly 30 by a surgeon with a grasper.

Referring to FIGS. 12 and 13, removable trocar 157 includes a trocar tip 157*a*, a body portion 157*b* and a cantilevered arm 157*c*. A projection 157*d* is positioned on the free end of cantilevered arm 157*c*. Arm 157*c* is deflectable downwardly, i.e., radially inwardly, in the direction indicated by arrow "A" in FIG. 13 to facilitate insertion of body portion 157*b* into bore 170 of center rod 154. Splines 157*e* or the like, preferably, are provided on body portion 157*b* to properly align trocar 157 within bore 170. Arm 157*c* biases projection 157*d* outwardly such that when projection 157*d* passes beneath opening 155*a* in center rod 154, projection 157*d* snaps outwardly into opening 155*a* to releasably secure removable trocar 157 to center rod 154. A tab 157*f* is positioned on arm 157*c* and can be engaged to depress arm 157*c* and projection 157*d* to remove projection 157*d* from an opening 155*a* of arm 155 to facilitate removal of trocar 157 from center rod 154. Trocar tip 157*a* includes a throughbore 157*g* dimensioned to receive a suture (not shown) to facilitate locating and removal of trocar 157 and/or anvil assembly 30 within and from the human body. Although illustrated as having a sharpened tip, other trocar tip configurations are envisioned, e.g., a blunt tip.

Shell Assembly

Referring to FIG. 6, shell assembly 31 includes a shell 182, a pusher back 186, a cylindrical knife 188, and a staple guide 192. Shell 182 includes an outer housing portion 194 and an inner guide portion 196 having grooves 196*a* for mating with splines 181 on anvil center rod 154 (FIG. 10). Outer housing portion 194 defines a throughbore 198 having a distal cylindrical section 200, a central conical section 202 and a proximal smaller diameter cylindrical section 204. A plurality of openings 206 are formed in conical section 202. Openings 206 are dimensioned to permit fluid and tissue passage during operation of the device. A pair of diametrically opposed flexible engagement members 207 are formed on proximal cylindrical section 204 of shell 182. Engagement members 207 are positioned to be received in openings 207*a* formed on the distal end of outer tube 14*a* to secure shell 182 to elongated body 14. A pair of openings 211 formed in the proximal end of outer tube 14*a* are dimensioned to receive protrusions (not shown) formed on the internal wall of stationary handle 18 to facilitate attachment of tube 14*a* to handle portion 12.

Pusher back 186 includes a central throughbore 208 which is slidably positioned about inner guide portion 196 of shell 182. Pusher back 186 includes a distal cylindrical section 210 which is slidably positioned within distal cylindrical section 200 of shell 182, a central conical section 212 and a proximal smaller diameter cylindrical section 214. The proximal end of pusher back 186 includes members 220 which are configured to lockingly engage with resilient fingers 110 of pusher link 74 to fasten pusher link 74 to pusher back 186 such that a distal face of pusher link 74 abuts a proximal face of pusher back 186.

The distal end of pusher back 186 includes a pusher 190. Pusher 190 includes a multiplicity of distally extending fingers 226 dimensioned to be slidably received within slots 228 formed in staple guide 192 to eject staples 230 therefrom. Cylindrical knife 188 is frictionally retained within the central throughbore of pusher back 186 to fixedly secure knife 188 in relation to pusher 190. Alternately, knife 188 may be retained within pusher back 186 using adhesives, crimping, pins, etc. The distal end of knife 188 includes a circular cutting edge 234.

In operation, when pusher link 74 is advanced distally in response to actuation of firing trigger 20, as will be described below, pusher back 186 is advanced distally within shell 182. Advancement of pusher back 186 advances fingers 226 through slots 228 of staple guide 192 to advance staples 230 positioned within slots 228 and eject staples 230 from staple guide 192 into staple deforming pockets 140 of anvil 129. Since knife 188 is secured to pusher back 186, knife 188 is also advanced distally to core tissue as will be described in more detail below.

Figure 14:
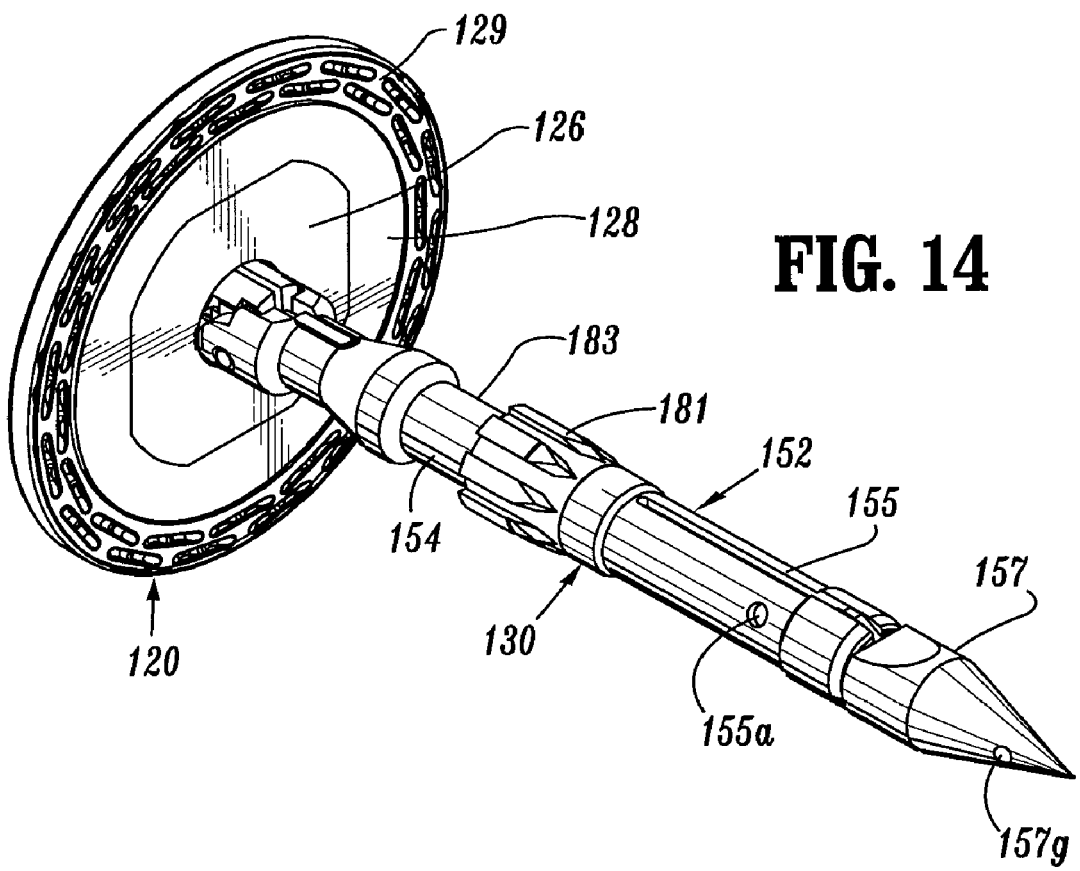
FIG. 14 is a side perspective view from the proximal end of the anvil assembly shown in FIG. 10 with the removable trocar attached thereto.
Figure 15:
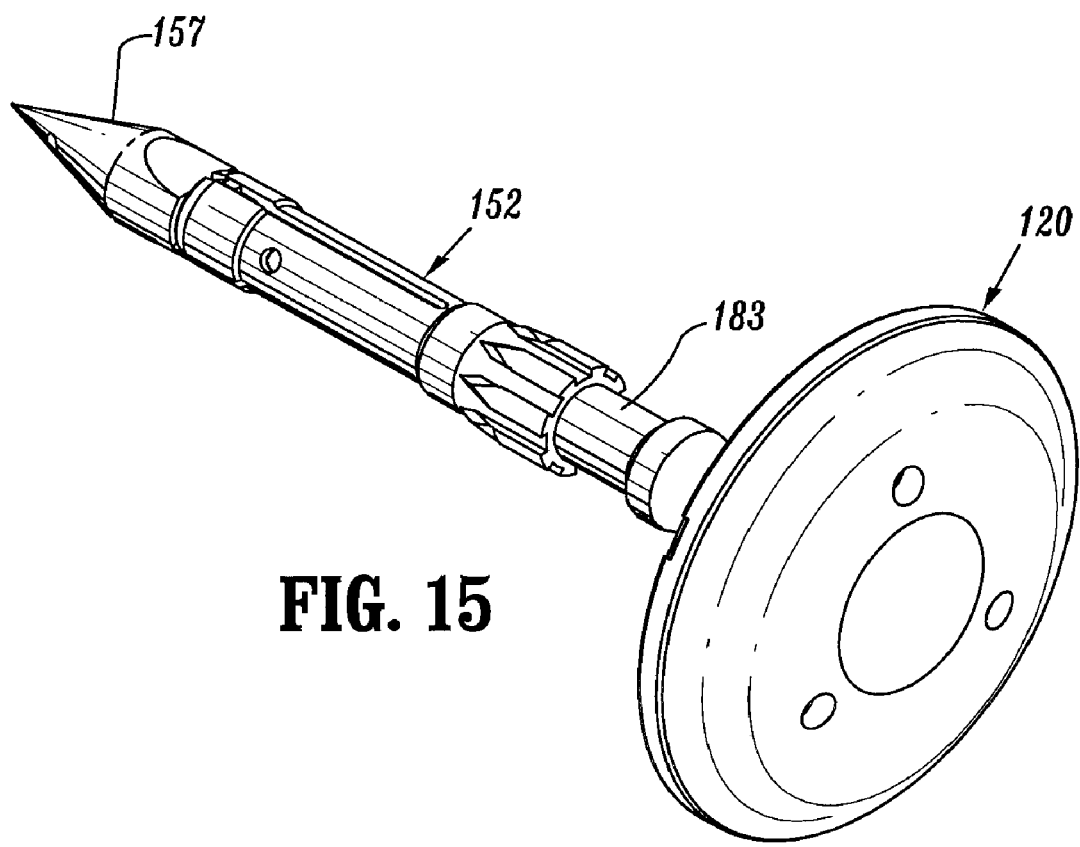
FIG. 15 is a side perspective view from the distal end of the anvil assembly shown in FIG. 14.
Figure 16:
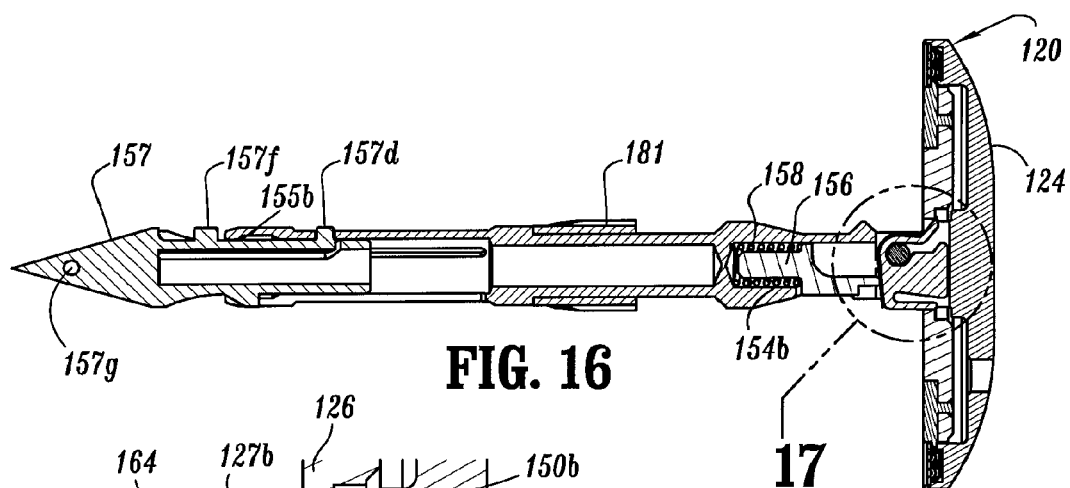
FIG. 16 is a side cross-sectional view taken through the retaining clip of the anvil assembly and removable trocar of the anvil assembly shown in FIG. 15.

A rigid bushing 209 is supported in the proximal end of inner guide portion 196 of shell 182. Bushing 209 defines a throughbore dimensioned to slidably receive anvil retainer 38 and center rod 154 of anvil assembly 30 (FIG. 14). Bushing 209 provides lateral support for flexible arms 155 of center rod 154 when the anvil assembly 30 has been approximated to prevent disengagement of anvil assembly 30 from anvil retainer 38. In the unapproximated position, flexible arms 155 of center rod 154 are positioned externally of bushing 209 to permit removal of anvil assembly 30 from retainer 38.

Cam Adjustment Mechanism

Referring to FIGS. 8 and 22-28, a cam adjustment member 400 is secured by set screw 312 onto a sidewall 306a of screw stop 306 within a recess 306b formed in sidewall 306a. Cam adjustment member 400 includes a circular disc 402 having a throughbore 404. Throughbore 404 is eccentrically formed through disc 402 and is dimensioned to receive set screw 312. A smaller notch or hole 406 is also formed in disc 402 and is dimensioned to receive the tip of an adjustment tool (not shown). Recess 306b (FIG. 22) includes a forward abutment shoulder or surface 306c and a rear abutment surface 306d and is dimensioned to receive disc 402 such that the outer edge of disc 402 abuts forward and rear abutment surfaces 306c and 306d.

Set screw 312 extends through disc 402 and screw stop 306 and is received in a threaded bore 32a (FIG. 6) in screw 32 to secure screw stop 306 in an axially fixed position on screw 32. Cam adjustment member 400 functions to adjust the axial position of screw stop 306 on screw 32. More specifically, set screw 312 can be loosened to allow disc 402 to rotate within recess 306b of screw stop 306. Since disc 402 is eccentrically mounted about screw 32 and engages forward and rear abutment surfaces 306c and 306d of recess 306b, rotation of disc 402 about fixed set screw 312 will urge screw stop 306 axially along screw 32 to adjust the axial position of screw stop 306 on screw 32. For example, when disc 402 is rotated in a clockwise direction (as viewed in FIG. 28) as indicated by arrow "B", screw stop 306 will be moved axially in relation to screw 32 in the direction indicated by arrow "C" in response to engagement between the outer edge of disc 402 and rear shoulder 306d of recess 306b. Conversely, when disc 402 is rotated in a counter-clockwise direction (as viewed in FIG. 27), as indicated by arrow "D", screw stop 306 will be moved axially in relation to screw 32 in the direction indicated by arrow "E" in response to engagement between the outer edge of disc 402 and forward shoulder 306c of recess 306b.

When stapling device 10 is in a fully approximated position, i.e., anvil assembly 30 and shell assembly 31 are brought into juxtaposed alignment to define a tissue receiving clearance (FIG. 46), screw stop 306 abuts against body portion 42 of the rotatable sleeve 33, i.e., sleeve 33 functions as a stop for the approximation mechanism. See FIG. 48. In this position, anvil assembly 30 and shell assembly 31 are spaced slightly to define a tissue receiving clearance. By providing cam adjustment member 400, the tissue receiving clearance can be selectively adjusted to be within a desired range by adjusting the position of screw stop 306 on screw 32. Preferably, cam adjustment member 400 permits adjustment of the tissue receiving clearance of ±0.045 inches, although greater or lesser adjustment capabilities are also envisioned. Typically, adjustments to the tissue receiving clearance will be made by the device manufacturer. Alternately, a hole or opening may be provided in handle portion 12 (FIG. 1) to provide direct access to adjustment member 400 to allow for on-site adjustment of the tissue receiving clearance by a surgeon or other medical professional.

Indicator Mechanism

Figure 32:
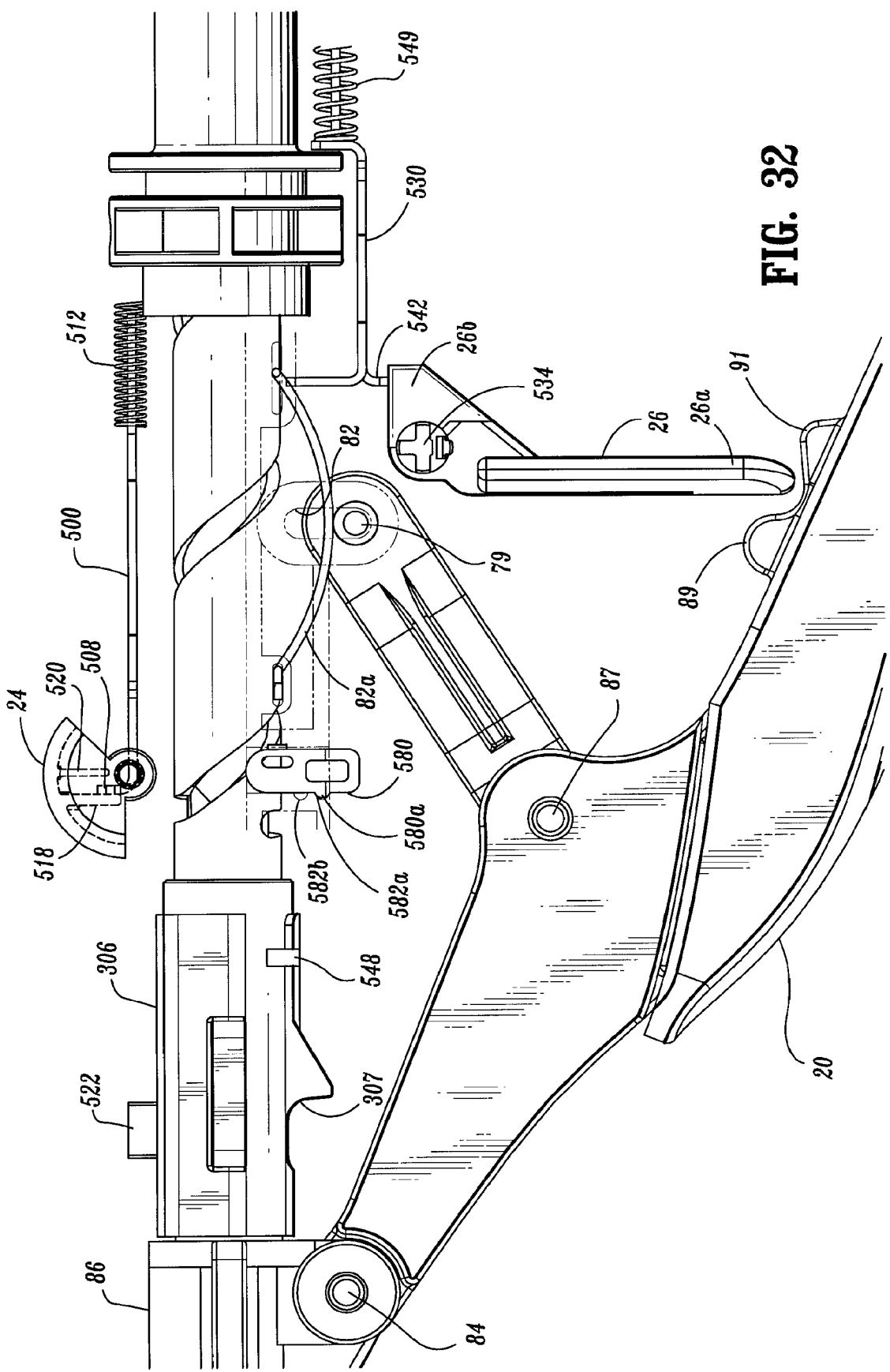
FIG. 32 is a side enlarged view of the handle assembly of the surgical stapling device shown in FIG. 31 with the handle sections removed.

Referring to FIGS. 3-5 and 29, the indicator mechanism includes bulbous indicator 24, lens cover 24a and slide member 500. Indicator 24 is pivotally supported about a pivot member 502 which is preferably formed monolithically with handle sections 18a and 18b. Lens cover 24a is positioned above indicator 24 and is preferably formed of magnification material to facilitate easy visualization of indicator 24. Slide member 500 includes a body portion 504 having a elongated slot 506 formed therein, a distal abutment member or upturned lip portion 508, and a proximal extension 510. Slide member 500 is slidably positioned between handle sections 18a and 18b. Proximal extension 510 is slidably supported within stationary handle 18 by support structure 516 (FIG. 5) which may be integrally formed with handle sections 18a and 18b. A biasing member, preferably a coil spring 512, is positioned in compression about proximal extension 510 between support structure 516 and body portion 504 of slide member 500 to urge slide member 500 distally within stationary handle 18. Indicator 24 includes a pair of downwardly extending projections 518 and 520 (FIG. 32). Upturned lip portion 508 of slide member 500 is positioned between projections 518 and 520 and is positioned to engage projections 518 and 520 as it moves within stationary handle 18. In the unfired position of device 10, biasing member 512 urges slide member 500 distally to move lip portion 508 into engagement with projection 518 to pivot indicator to a first position, which provides indication to a surgeon that the device has not been approximated and is not in a fire-ready condition.

Figure 33:
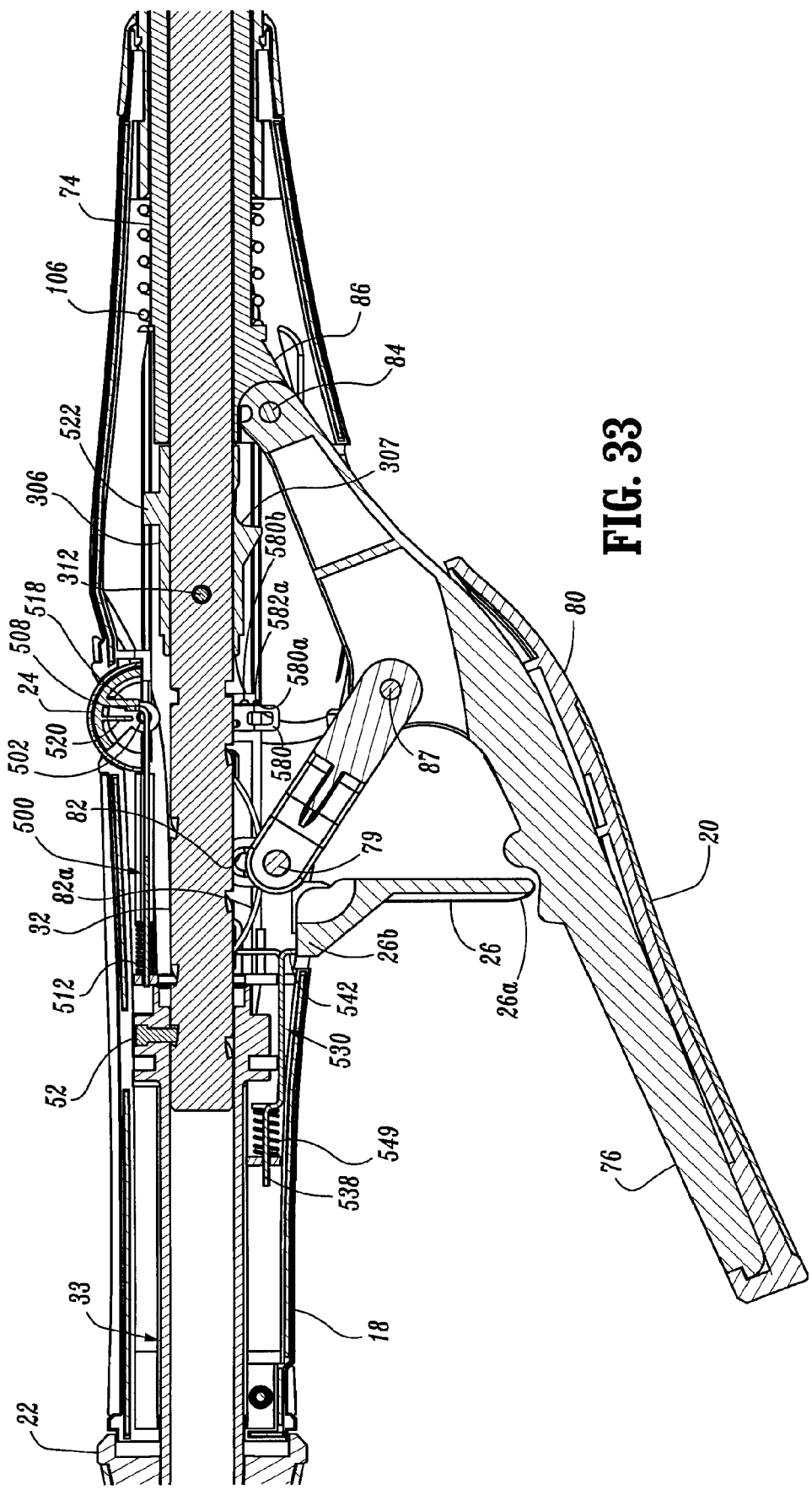
FIG. 33 is an enlarged view of the indicated area of detail shown in FIG. 31.
Figure 34:
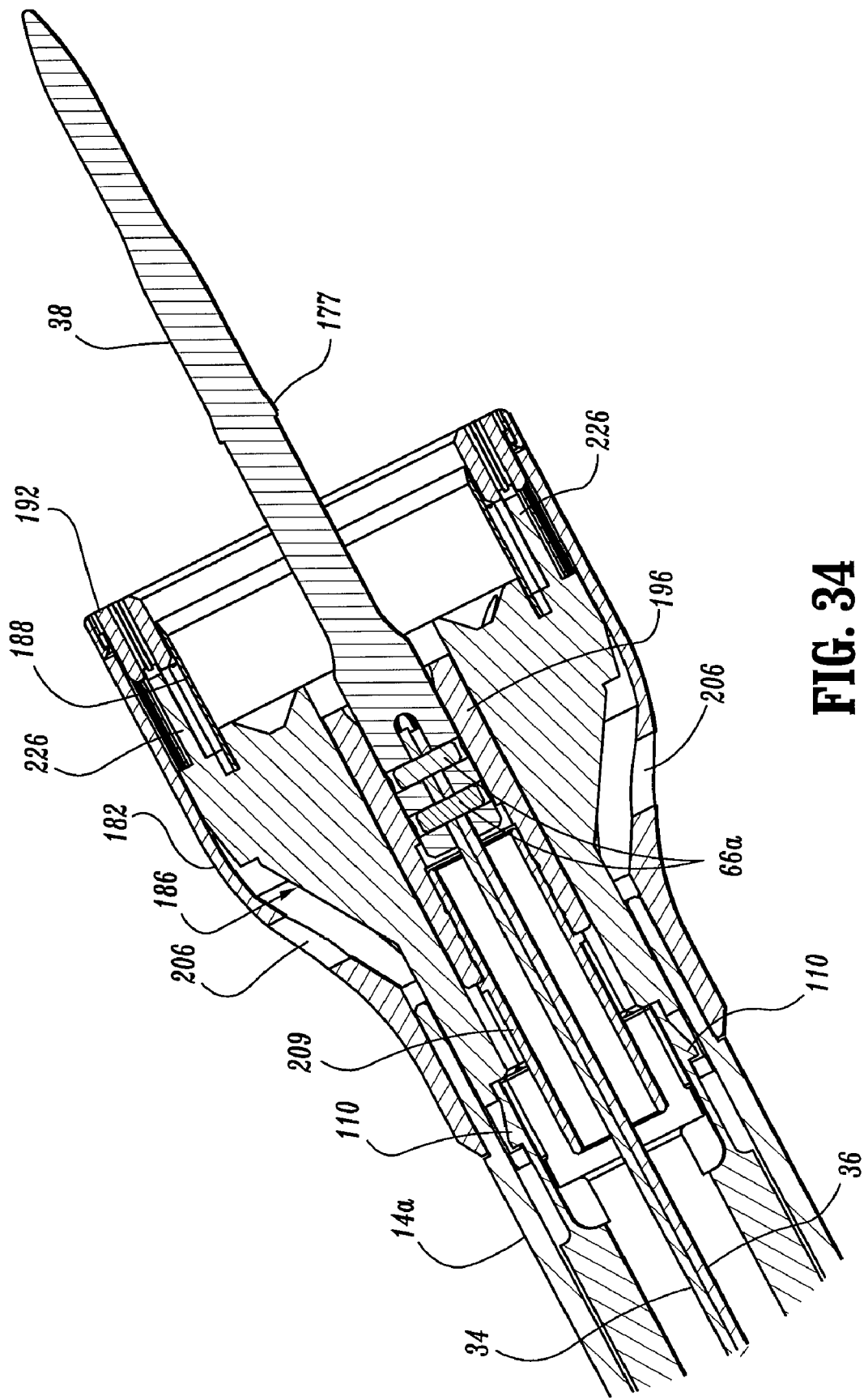
FIG. 34 is an enlarged view of the indicated area of detail shown in FIG. 31.
Figure 35:
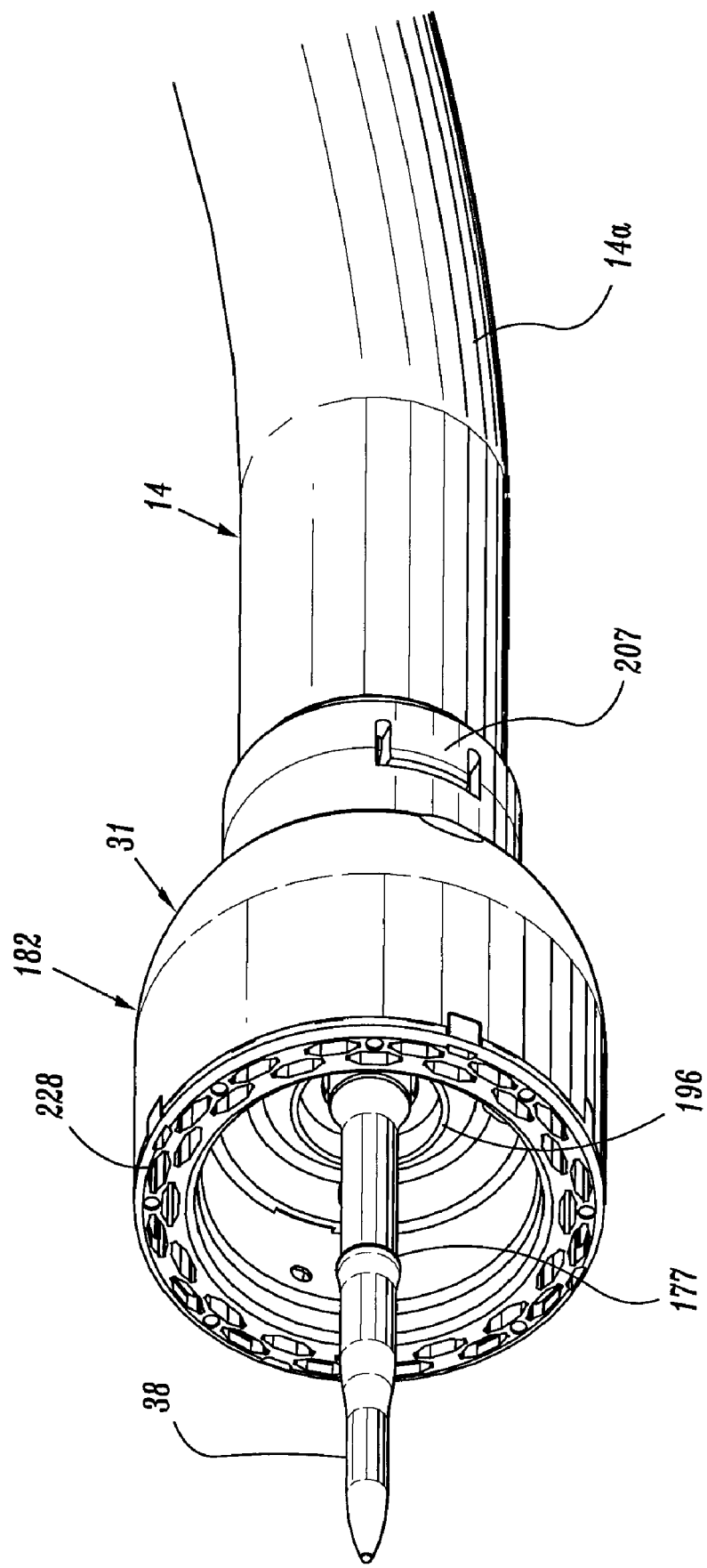
FIG. 35 is a perspective view from the front of the distal end of the surgical stapling device shown in FIG. 31 with the anvil assembly removed.

As discussed above, screw stop 306 is fixedly attached to screw 32 (FIG. 33). Screw stop 306 includes a first abutment or engagement member 522 which is positioned to travel through slot 506 of slide member 500 and engage the proximal end 506a (FIG. 29) of slot 506 during approximation of the device. When engagement member 522 abuts proximal end 506a of slot 506, further approximation of device 10 moves slide plate 500 proximally within stationary handle 18 against the bias of spring 512 such that upturned lip 508 of slide member 500 engages projection 520 of indicator 24. Engagement between projection 520 and lip 508 causes indicator 24 to pivot about pivot member 502 to a second position. In the second position, indicator 24 provides indication to a surgeon that the device has been approximated and is now in a fire-ready position. See FIG. 48.

Fire-Lockout Mechanism

Referring to FIGS. 3-5, and 30, the firing-lockout mechanism includes trigger lock 26 and a lockout member 530. Trigger lock 26 is pivotally supported within bores 532 (FIG. 3) in handle sections 18a and 18b about pivot member 534. Pivot member 534 is preferably T-shaped and frictionally engages the inner wall of bores 532 to prevent free rotation of trigger lock 26. Alternately, other pivot member configurations are envisioned, e.g., circular, square, etc. Tip 26a of trigger lock 26 is positioned between abutments 89 and 91 on body portion 76 of firing trigger 20 to prevent actuation of trigger 20 when trigger lock 26 is in the locked position. Trigger lock 26 also includes a proximal extension 26b which will be discussed in further detail below.

Lockout member 530 includes a body portion 536, a proximal extension 538, a pair of front legs 540a, a pair of rear legs 540b, and an abutment member or downturned lip portion 542. Lockout member 530 is slidably positioned between first and second stops 544 and 546 (FIG. 5) formed on an internal wall of handle sections 18a and 18b. Stop 544 is positioned to engage rear legs 540b and stop 546 is positioned to engage front legs 540a. It is also envisioned that a single abutment member may be substituted for each pair of legs. A biasing member, preferably a coil spring 549, is positioned between stop 544 and body 536 about proximal extension 538 to urge lockout 530 to its distal-most position with legs 540 abutting stop 546. In this position, extension 26b of trigger lock 26 is positioned beneath lip portion 542 of lockout member 530 to prevent pivotal movement of trigger lock 26 about pivot member 534, and thus prevent firing of stapling device 10.

Figure 23:
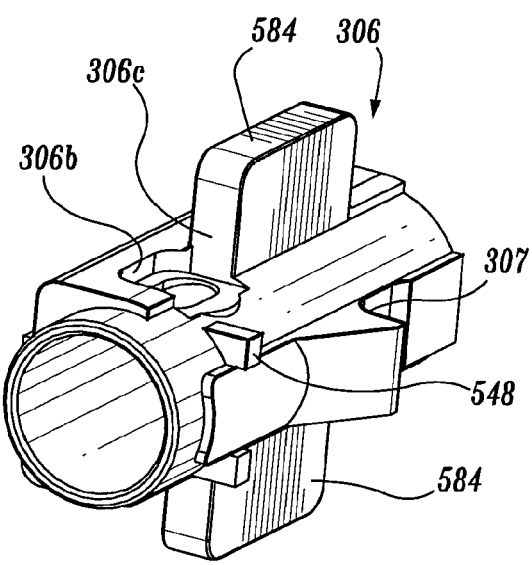
FIG. 23 is a bottom perspective view from the proximal end of the screw stop shown in FIG. 22.
Figure 24:
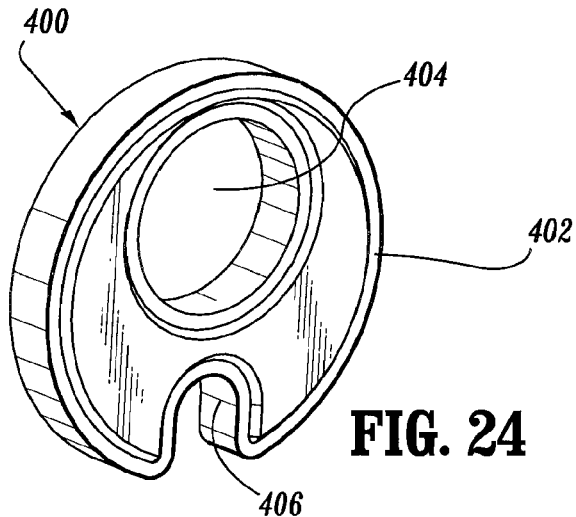
FIG. 24 is a top perspective view of the cam adjustment member of the handle assembly shown in FIG. 3.
Figure 25:
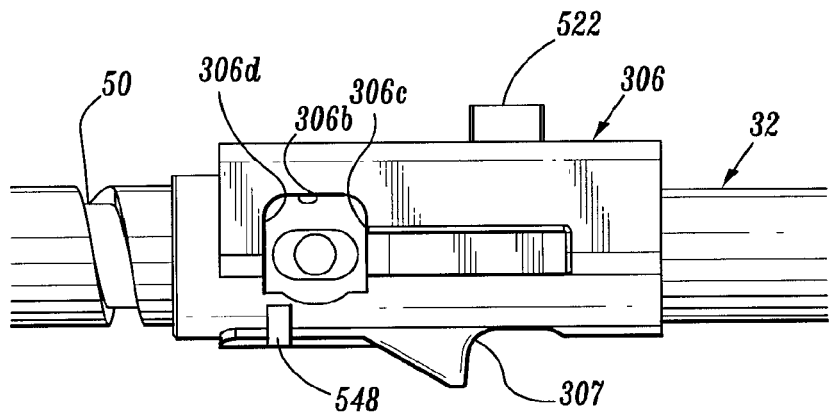
FIG. 25 is a side view of the screw and screw stop of the handle assembly shown in FIG. 3 with the set screw and cam adjustment member removed.
Figure 26:
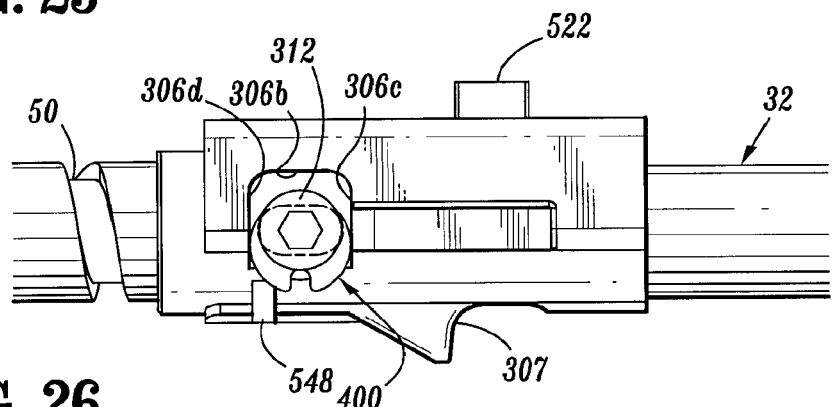
FIG. 26 is a side view of the screw and screw stop shown in FIG. 25 with the set screw and cam adjustment member attached thereto.
Figure 27:
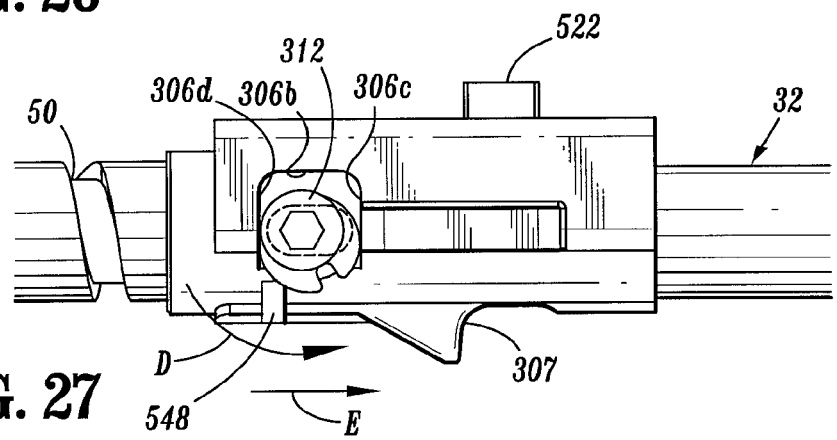
FIG. 27 is a side view of the screw and screw stop shown in FIG. 26 with the cam adjustment screw adjusted to increase the tissue gap.
Figure 28:
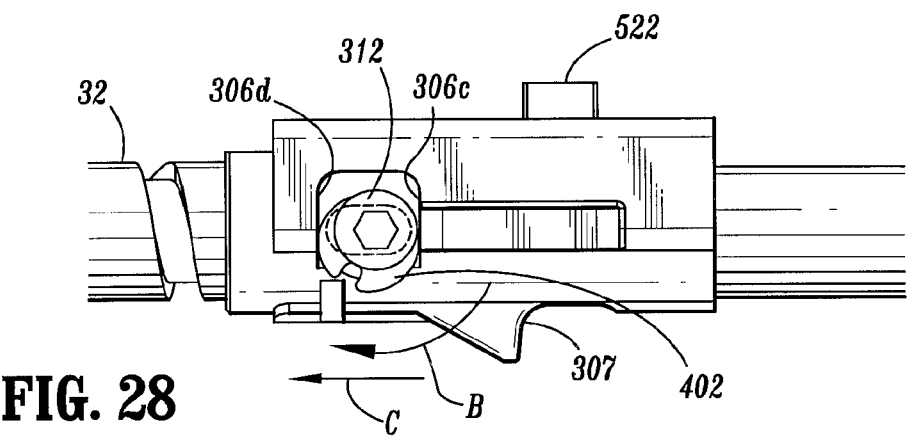
FIG. 28 is a side view of the screw and screw stop shown in FIG. 26 with the cam adjustment screw adjusted to decrease the tissue gap.
Figure 29:
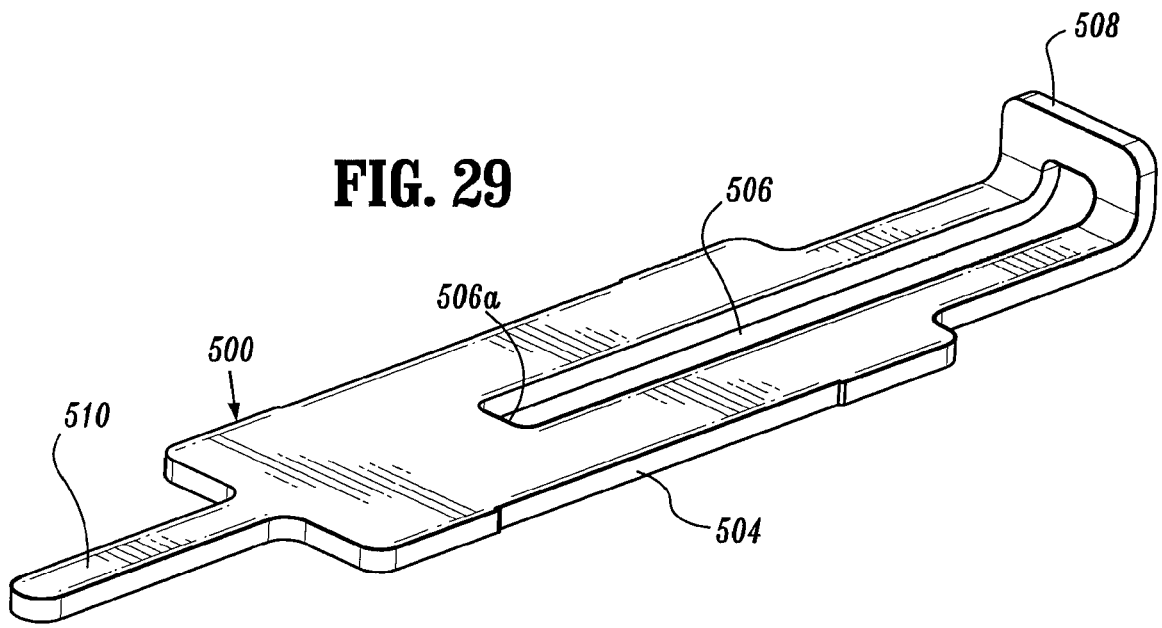
FIG. 29 is a top perspective view from the proximal end of the slide member of the indicator mechanism of the handle assembly shown in FIG. 3.
Figure 30:
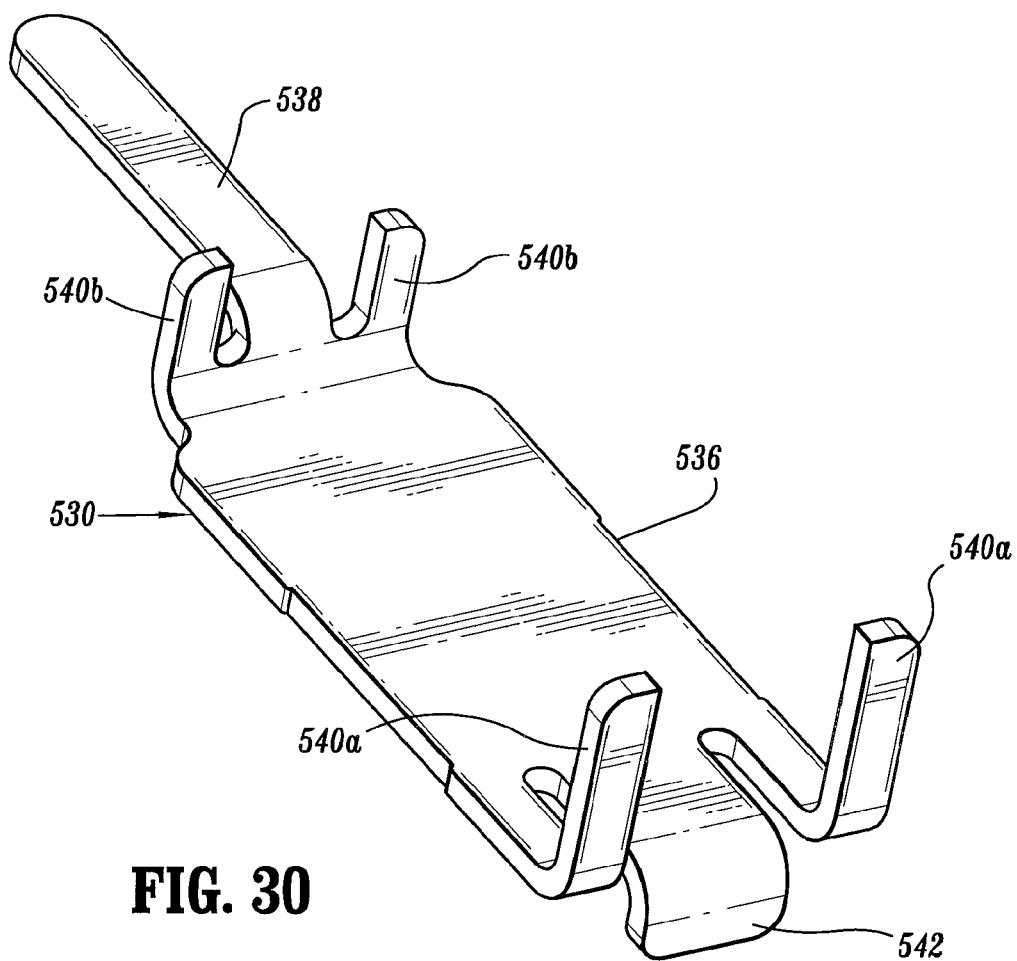
FIG. 30 is a bottom perspective view of the lockout member of the fire lockout mechanism of the handle assembly shown in FIG. 3.
Figure 31:
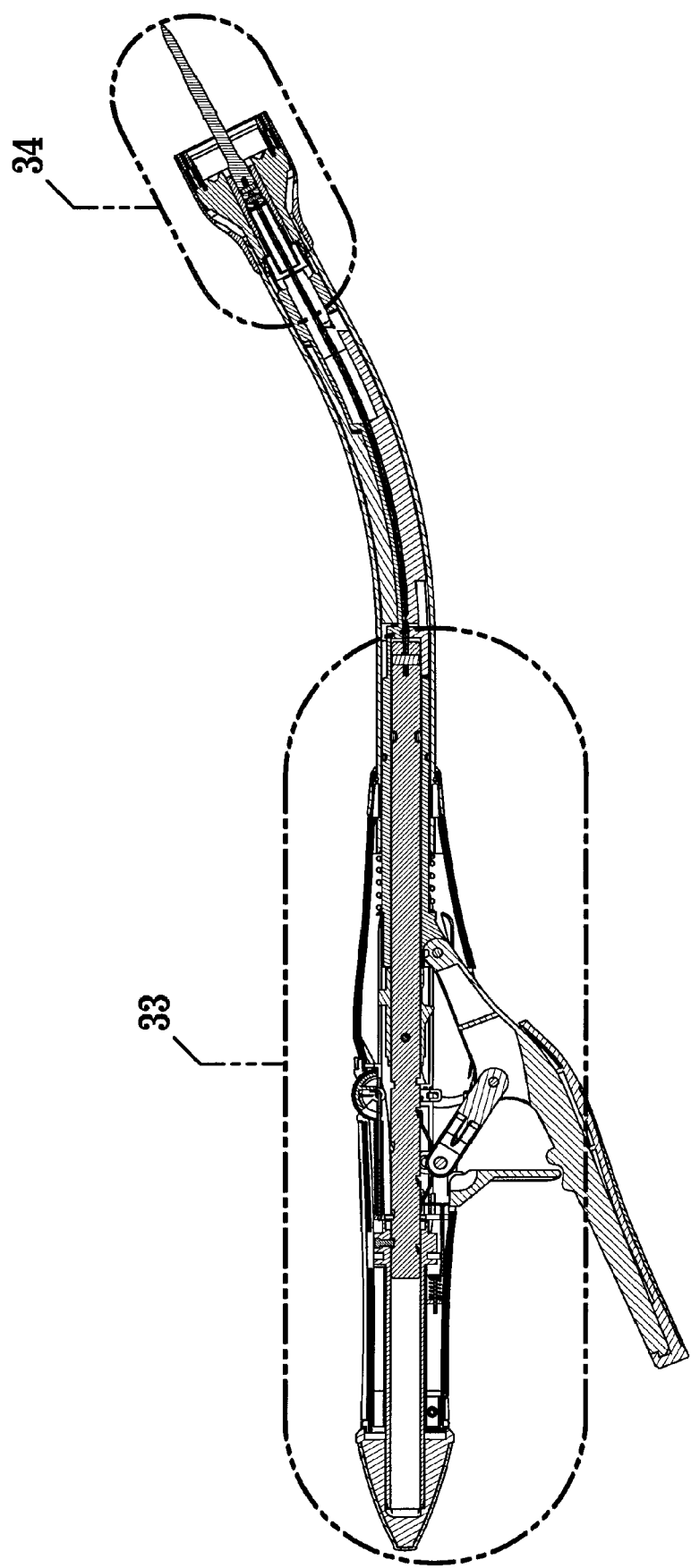
FIG. 31 is a side cross-sectional view of the surgical stapling device shown in FIG. 1 with the anvil assembly removed.

As discussed above, screw stop 306 is secured to screw 32. A second engagement member or members 548 extend downwardly from screw stop 306 (FIG. 23). When stapling device 10 is approximated and screw 32 is moved proximally within stationary handle 18, engagement member 548 abuts distal legs 540a (FIG. 47) of lockout member 530 to move lockout member 530 proximally against the bias of spring member 549 to a position in which lip portion 542 is spaced proximally of extension 26b of trigger lock 26. In this position of lockout member 530, trigger lock 526 can be pivoted about pivot member 534 to permit firing of stapling device 10.

Tactile Indicator Mechanism

Referring to FIGS. 3, 5, 9 and 9A, a tactile indicator mechanism provided in stationary handle 18 includes an abutment member 580 which is slidably positioned in a vertical slot 582 defined within handle sections 18a and 18b. Abutment member 580 includes a protuberance 580a and a guide rib 580b. Protuberance 580a is dimensioned to be received within one of two detents 582a and 582b formed along a wall of slot 582. Abutment member 580 is movable from a retracted (downward) position, wherein protuberance 580a is positioned within detent 582a, to an extended (upward) position, wherein protuberance 580a is positioned within detent 582b. Engagement between protuberance 580a and detents 582a and 582b retains abutment member 580 in its respective upward or downward position.

Prior to firing of stapling device 10, abutment member 580 is located in the retracted (downward) position. When device 10 is fired, an extension 590 (FIG. 3) of firing link 72 engages abutment member 580 and moves abutment member 580 from its retracted to its extended position. In the extended position, abutment member 580 extends into channel 111 of stationary handle 18.

Screw stop 306 includes a pair of wings 584 which are slidably positioned in channel 111 of stationary handle 18. After stapling device 10 has been fired, abutment member 580 is positioned within channel 111. During unapproximation of anvil assembly 30 and cartridge assembly 31, a wing 584 of screw stop 306 will engage abutment member 580 and urge abutment member 580 back to its retracted (downward) position. Engagement between abutment member 580 and wing 584 of screw stop 306 provides a tactile and/or an audible indication to the surgeon that the anvil and cartridge assemblies 30 and 31 have been unapproximated a predetermined amount. Preferably, abutment member 580 is positioned to engage wing 584 of screw stop 306 at the point when the anvil and cartridge assemblies have been separated a distance sufficient to allow the anvil head assembly to tilt. Thus, engagement between abutment member 580 and wing 584 of screw stop 306 provides a tactile and/or audible indication to the surgeon that the anvil head assembly 120 has tilted and stapling device 10 can be removed from a patient.

Operation

Operation of surgical stapling device 10 will now be described in detail with reference to FIGS. 31-61.

FIGS. 31-35 illustrate surgical stapling device 10 in the unapproximated or open position prior to attachment of anvil assembly 30 to anvil retainer 38. In this position, biasing member 106 (FIG. 33) is engaged with coupling 86 to urge pusher link 74 to its proximal-most position in which coupling 86 abuts screw-stop 306. Biasing member 512 is engaged with slide member 500 of the indicator mechanism to position slide member 500 in engagement with projection 518 of indicator 24 to pivot indicator 24 in a clockwise direction, as viewed in FIG. 33. Biasing member 549 is engaged with body 536 of lockout member 530 to urge lockout member 530 to its distal-most position, wherein lip portion 542 of lockout member 530 is positioned above extension 26b of trigger lock 26 to prevent movement of trigger lock 26 to the unlocked position. Biasing member 82a is also engaged with pivot member 79 (FIG. 32) to urge pivot member 79 to the base of vertical slot 82 and tactile indicator 580 is in the retracted or downward position with protrusion 580a positioned with detent 582a.

Figure 38:
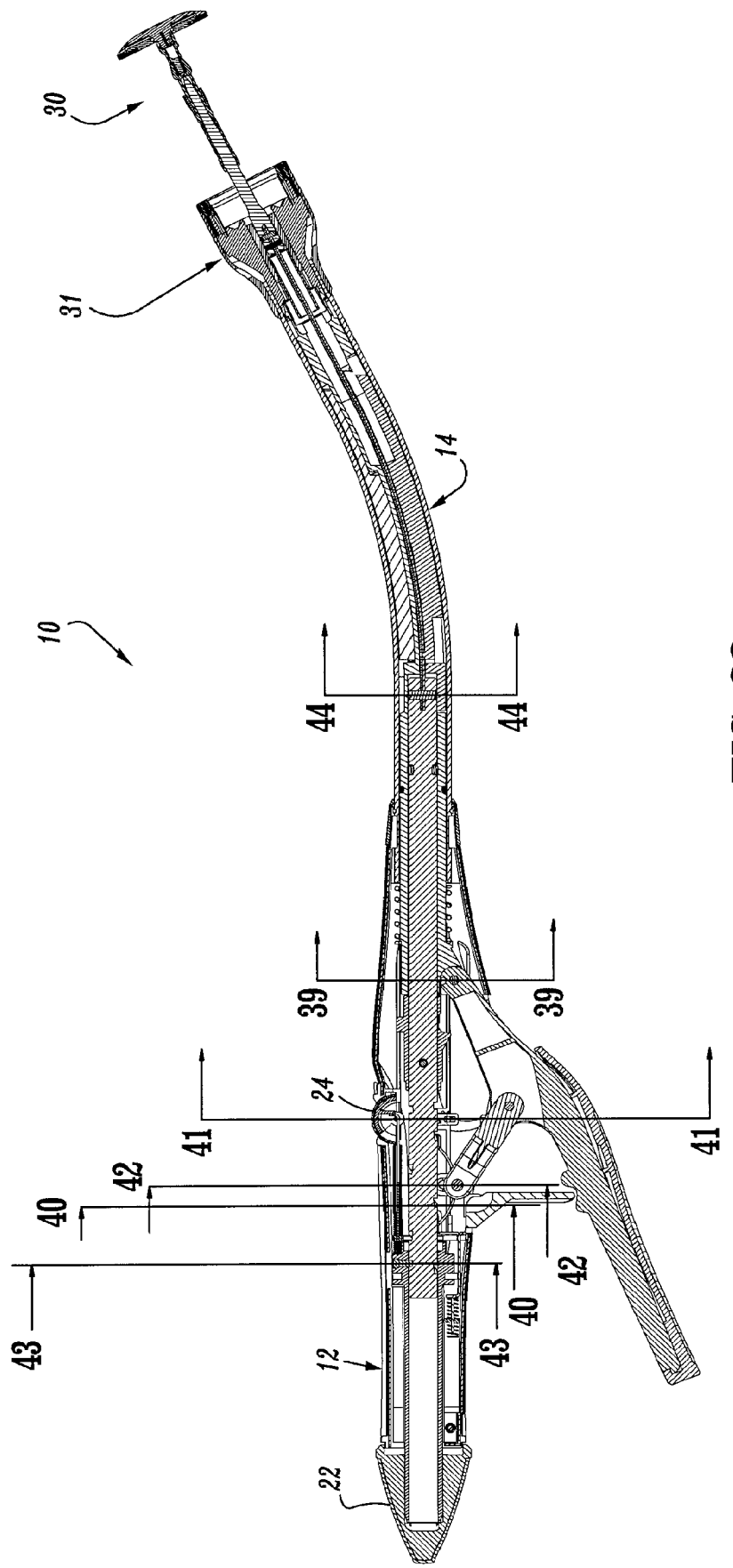
FIG. 38 is a side cross-sectional view of the surgical stapling device shown in FIG. 31 with the anvil assembly attached thereto.
Figure 45:
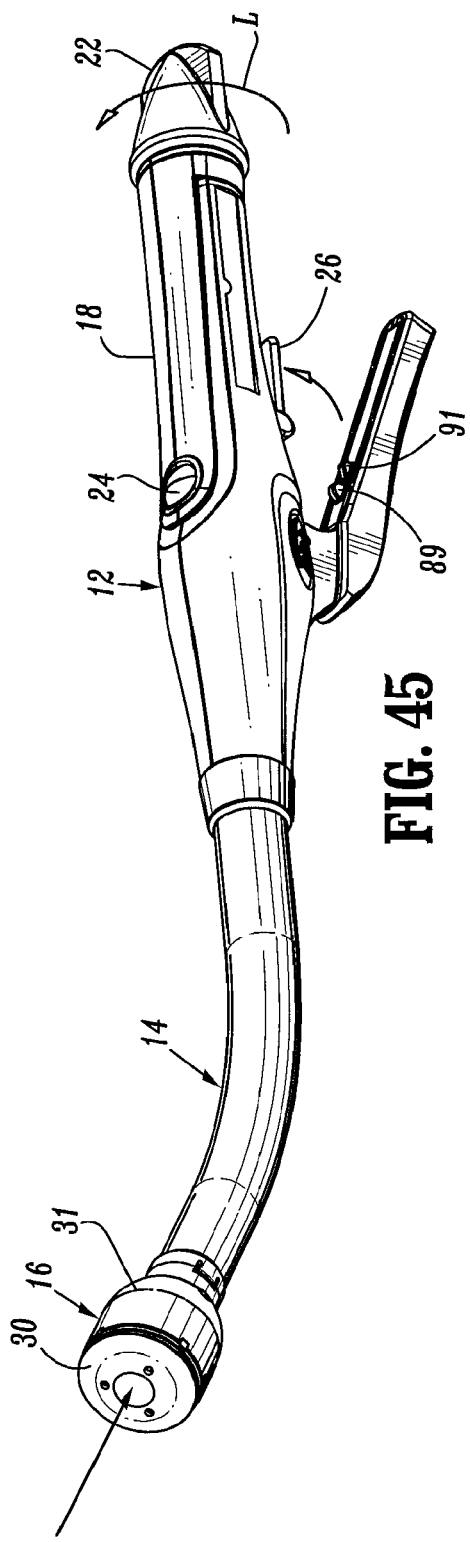
FIG. 45 is a side perspective view of the surgical stapling device shown in FIG. 38 with the anvil assembly in an approximated position.

FIGS. 36-44 illustrate surgical stapling device 10 with anvil assembly 30 attached to anvil retainer 38 and the anvil assembly 30 in the unapproximated or open position. Referring to FIGS. 37 and 38, during attachment of anvil assembly 30 to anvil retainer 38, anvil retainer 38 is positioned within bore 170 of center rod 154 of anvil assembly 30. Flexible arms 155 deflect outwardly to accommodate center rod 154. Center rod 154 is advanced onto anvil retainer 38 in the direction indicated by arrow "K" in FIG. 37 until internal shoulder 155b of flexible arms 155 passes over annular protrusion 177 formed on anvil retainer 38. At this point, resilient legs 155 releasably engage the anvil retainer. The position of the remaining components of stapling device are not affected by attachment of anvil assembly 30 to anvil retainer 38 and remain as described above and shown in FIGS. 31-35.

Figure 46:
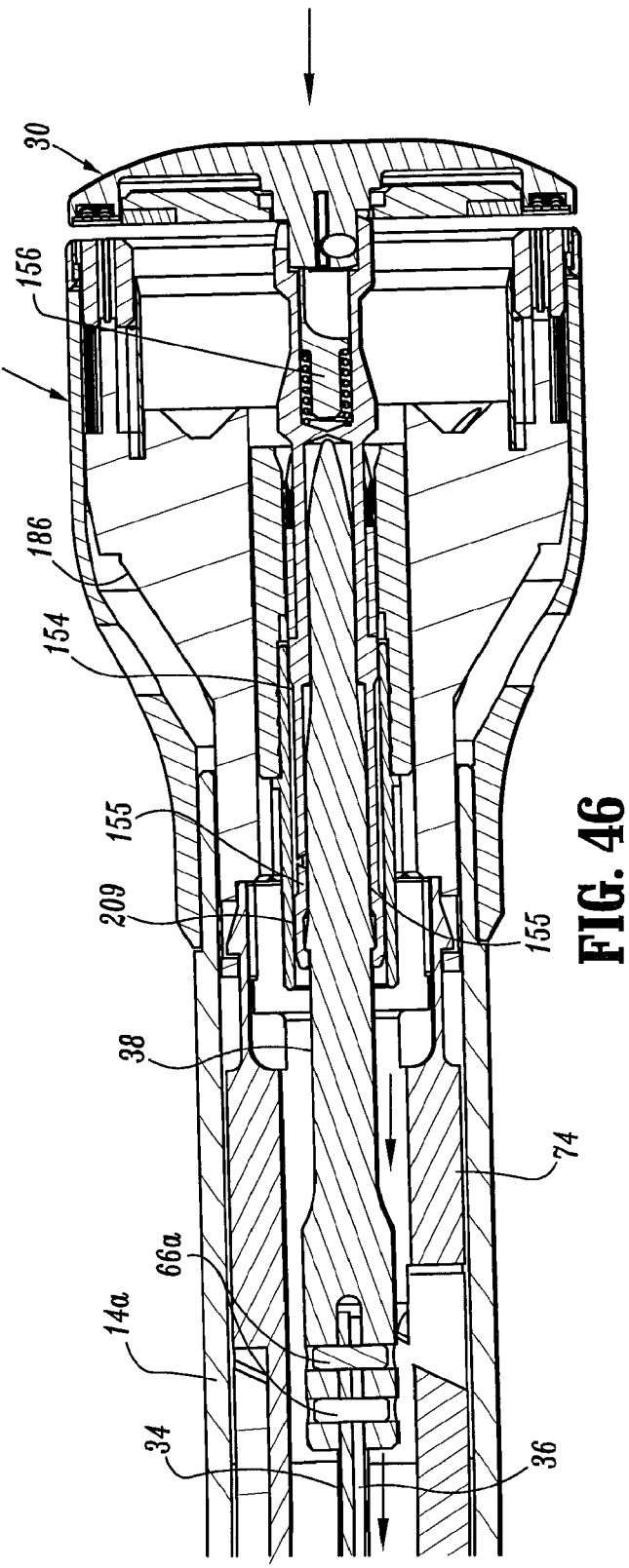
FIG. 46 is a side cross-sectional view of the distal end of the surgical stapling device shown in FIG. 45.

FIGS. 45-50 illustrate surgical stapling device 10 during movement of anvil assembly 30 and cartridge assembly 31 to the approximated or closed position. As discussed above, anvil assembly 30 is moved to the approximated or closed position by rotating rotation knob 22 in the direction indicated by arrow "L" in FIG. 45. Rotation of knob 22 causes cylindrical sleeve 33 to rotate to move pin 52 along helical channel 50 of screw 32. See FIG. 48. Movement of pin 52 along helical channel 50 causes screw 32 to translate proximally within sleeve 33. The distal end of screw 32 is connected to screw extensions 34 and 36 which are fastened at their distal ends to anvil retainer 38 (FIG. 46). As such, retraction of screw 32 within sleeve 33 is translated into proximal movement of anvil retainer 38 and anvil assembly 30. It is noted that when anvil assembly 30 is approximated, flexible legs 155 of center rod 154 are drawn into bushing 209 to lock legs 155 onto anvil retainer 38.

Figure 47:
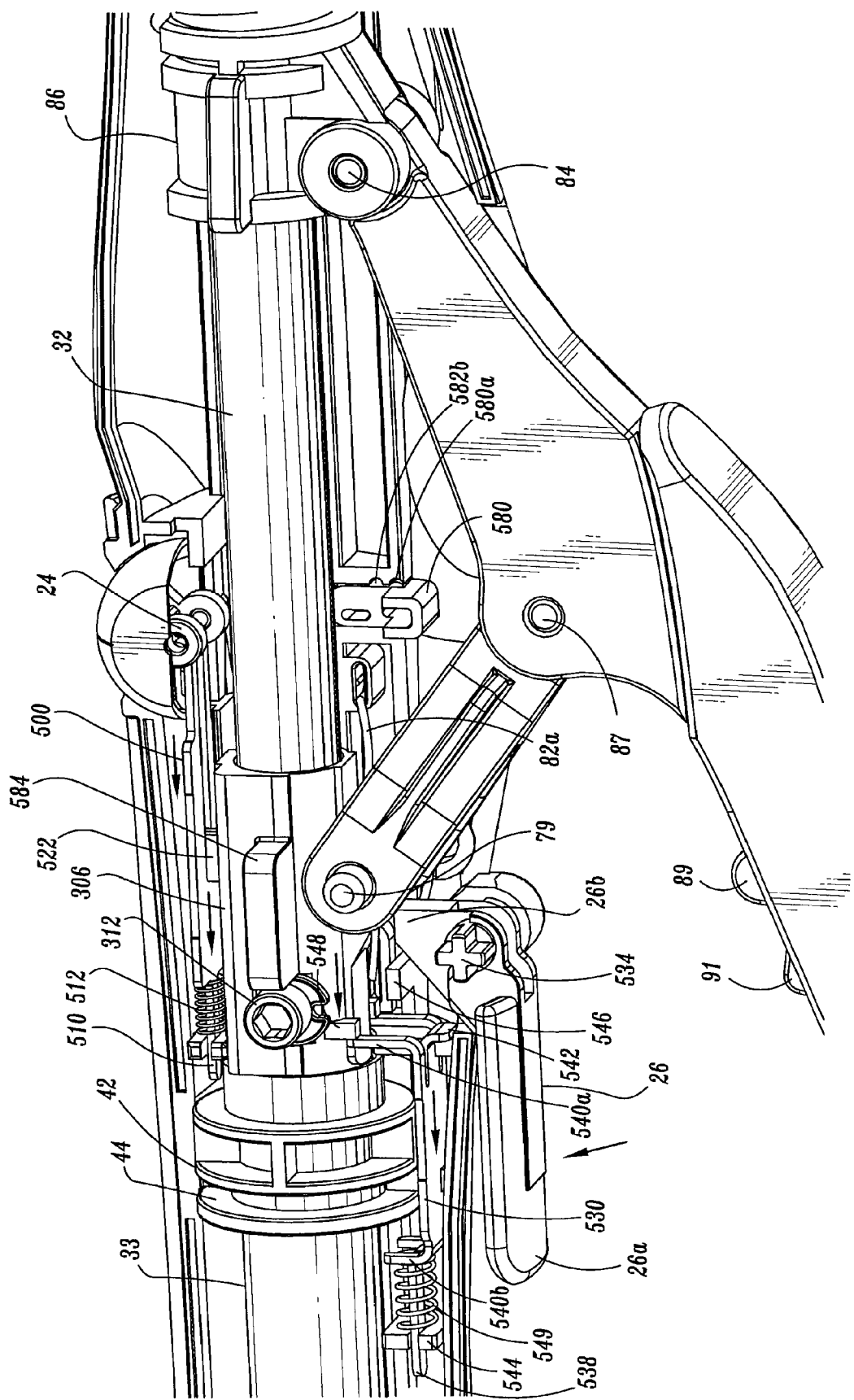
FIG. 47 is a side enlarged view of the handle assembly of the surgical stapling device shown in FIG. 45 with a handle section removed.
Figure 50:
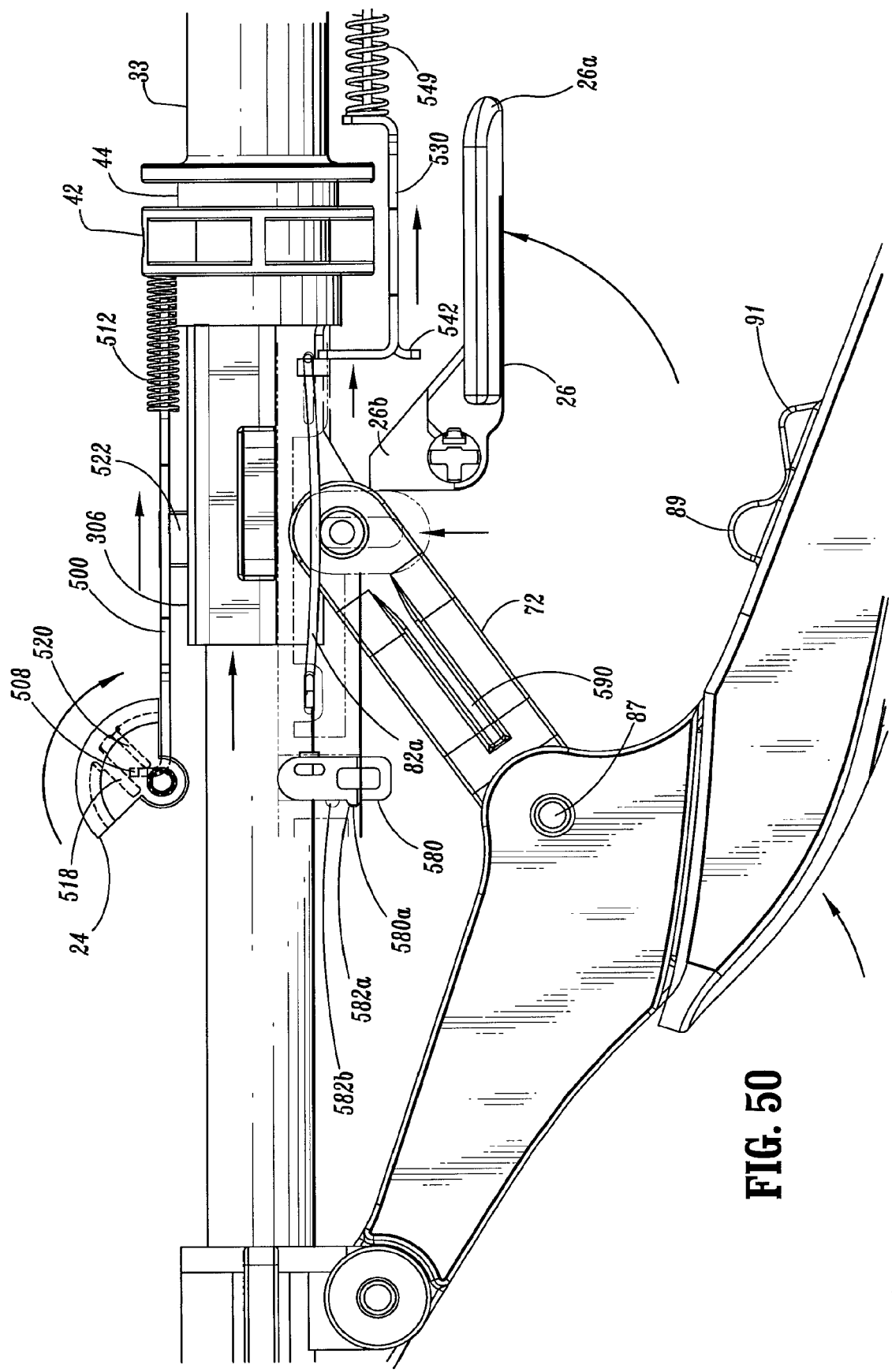
FIG. 50 is a side view of a portion of the handle assembly of the surgical stapler shown in FIG. 45 with the handle sections removed.
Figure 51:
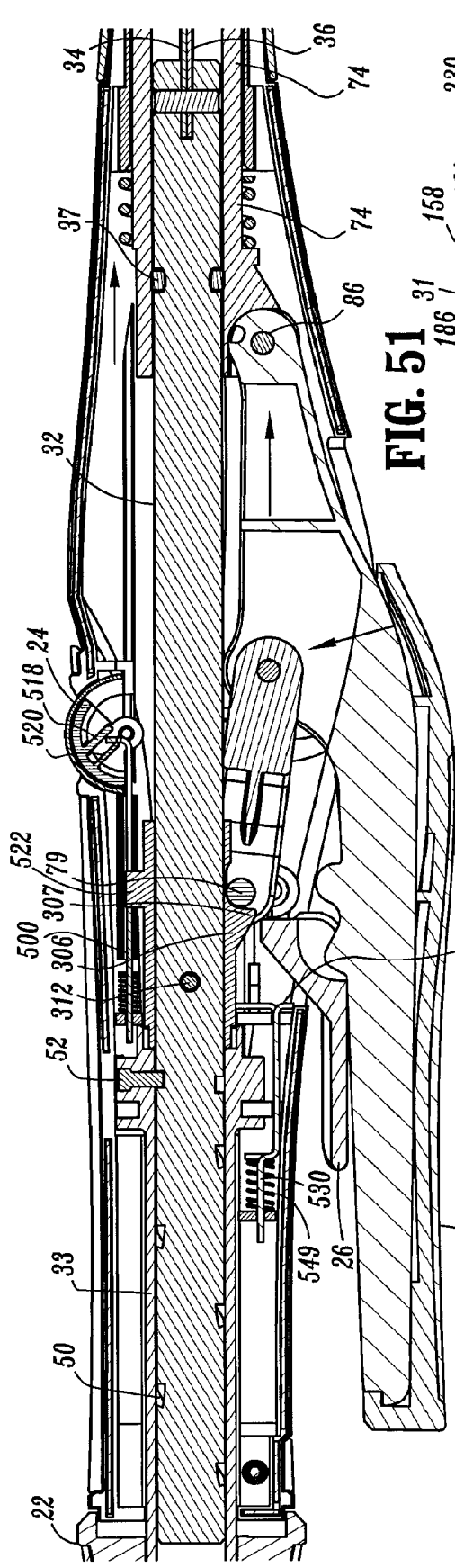
FIG. 51 is a side cross-sectional view of a portion of the handle assembly of the surgical stapling device shown in FIG. 45 after the firing trigger has been actuated.

Referring to FIGS. 47-49, screw stop 306 is axially fixed to screw 32 by set screw 312. Thus, as screw 32 is retracted within sleeve 33, screw stop 306 is moved from a distal position within stationary handle 18 to a proximal position. As screw stop 306 moves from the distal position to the proximal position, first engagement member 522 formed on screw stop 306 abuts proximal end 506a of slot 506 of slide plate 500 (FIG. 29) and moves slide plate 500 proximally against the bias of spring 512. As slide plate 500 moves proximally, lip 508 (FIG. 48) of slide member 500 engages projection 520 of indicator 24 to pivot indicator 24 in a counter-clockwise direction as viewed in FIG. 48.

Screw stop 306 also includes a second engagement member 548 (FIG. 47). As screw stop 306 is moved from the distal position to the proximal position during approximation of anvil assembly 30, second engagement member 548 engages distal legs 540a of lockout member 530 to move lockout member 530 proximally to a position in which lip portion 542 is spaced proximally of extension 26b of trigger lock 26. In this position, trigger lock 26 can be pivoted to an unlocked position to permit firing of stapling device 10.

Movement of screw stop 306 to its proximal-most position within stationary handle 18 positions abutment surface 307 of screw stop 306 in position to engage pivot member 79 of firing link 72. Abutment surface 307 comprises a substantially concave surface which is positioned to partially capture and act as a backstop for pivot 79 during firing of the stapling device.

Figure 52:
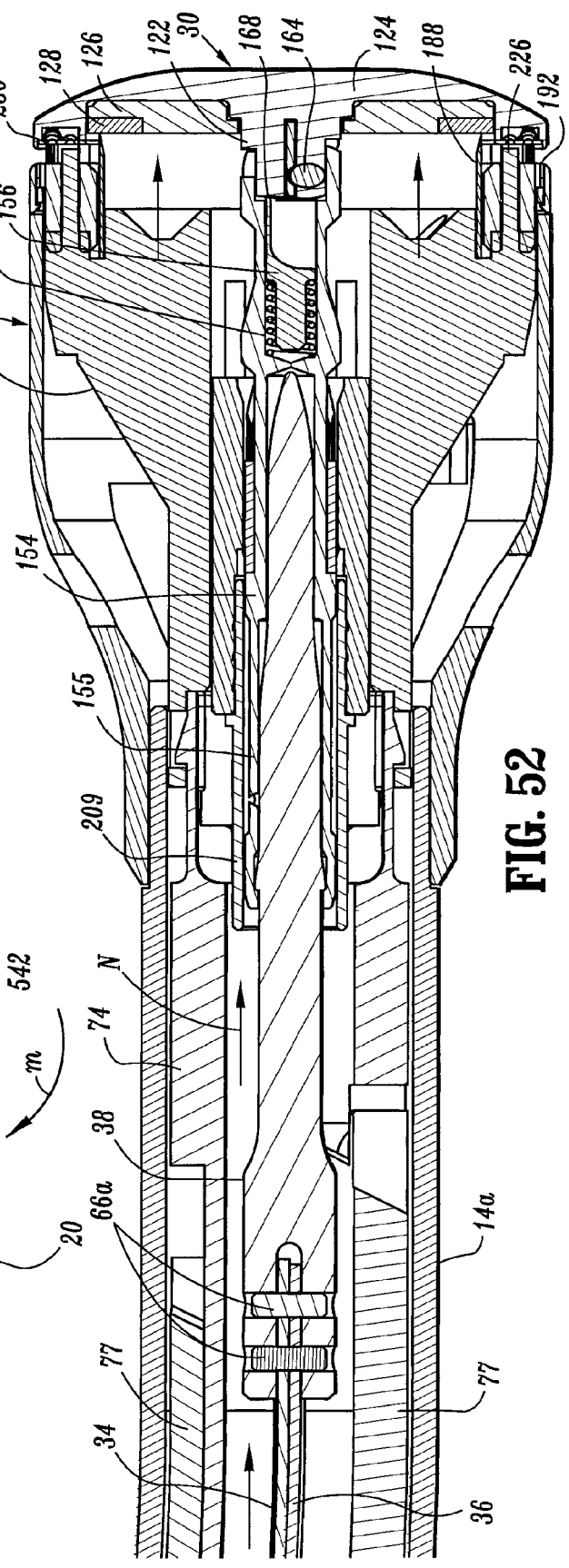
FIG. 52 is a side cross-sectional view of the distal end of the surgical stapling device shown in FIG. 45 after the firing trigger has been actuated.

FIGS. 51-56 illustrate surgical stapling device 10 during the firing stroke of firing trigger 20. As trigger 20 is compressed towards stationary handle 18 in the direction indicated by arrow "M" in FIG. 52, pivot member 79 engages abutment surface 307 on screw stop 306 and firing trigger 20 is pushed distally. As discussed above, the distal end of firing trigger 22 is connected through coupling member 86 to the proximal end of pusher link 74. Accordingly, as firing trigger 20 is moved distally, pusher link 74 is moved distally in the direction indicated by arrow "N" in FIG. 52 to effect advancement of pusher back 186 within shell assembly 31 (FIG. 52). Fingers 190 of pusher back 186 engage and eject staples 230 from staple guide 192.

Figure 56:
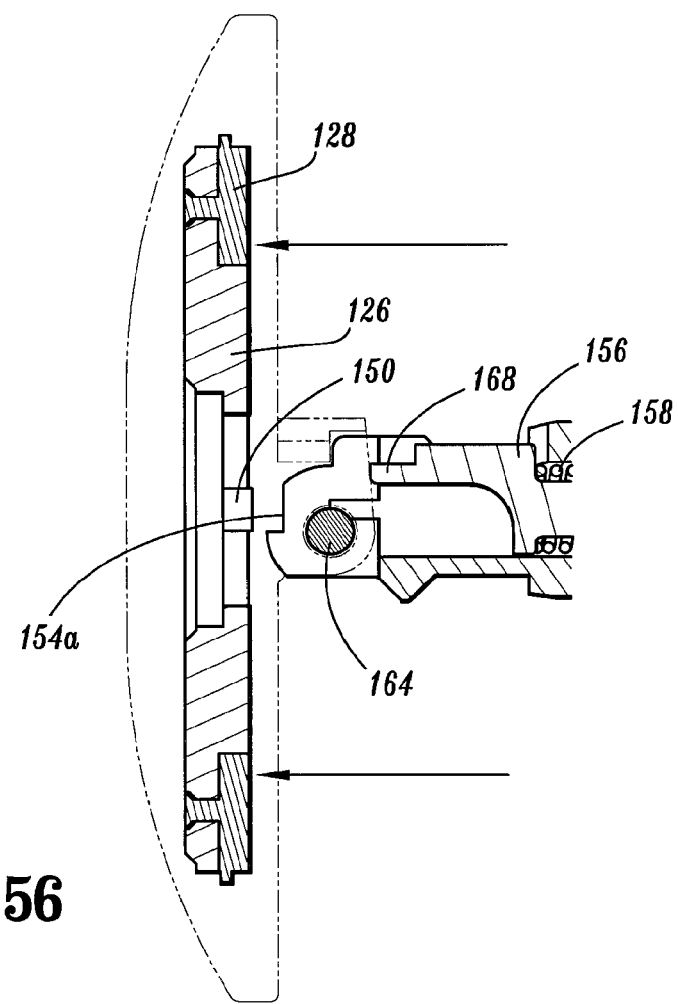
FIG. 56 is a side cross-sectional view of the distal portion of the anvil assembly shown in FIG. 55 with a portion of the anvil head assembly in phantom.
Figure 57:
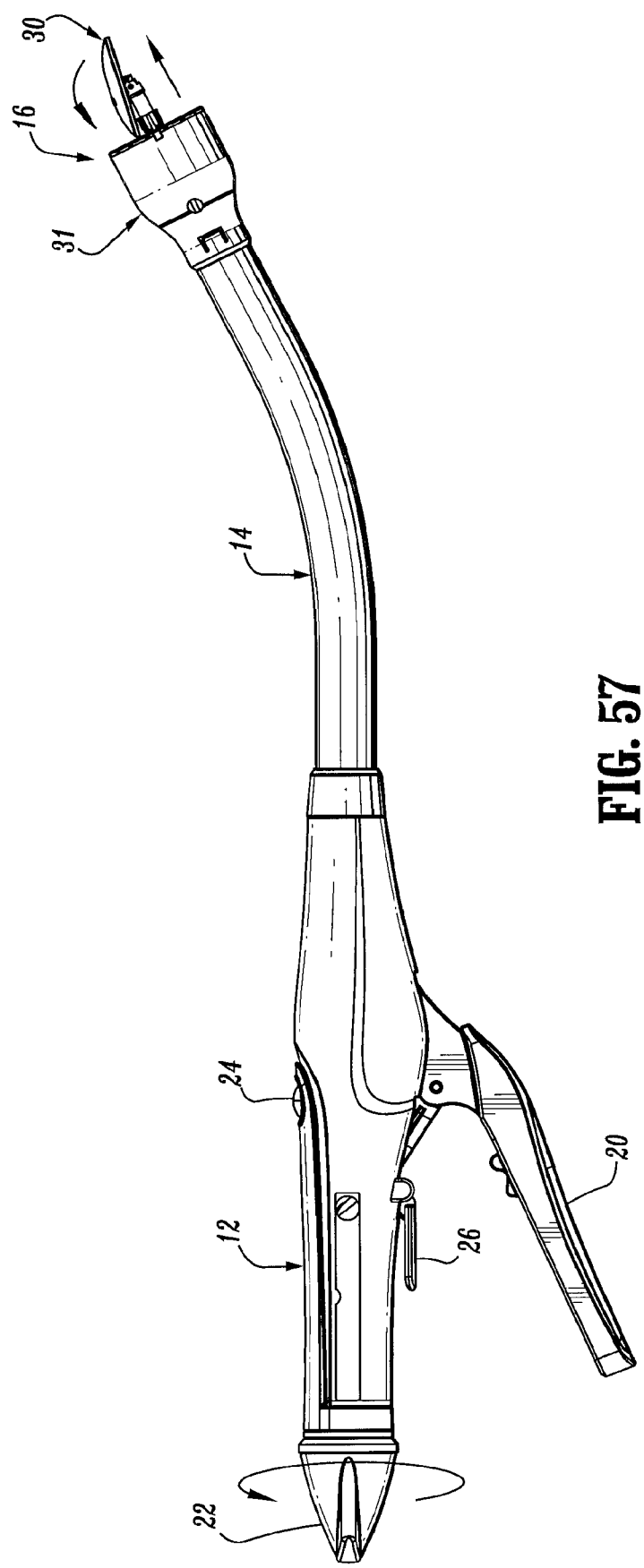
FIG. 57 is a side view of the surgical stapling device shown in FIG. 45 after the anvil assembly and cartridge assembly have been unapproximated a distance sufficient to permit the anvil head assembly to pivot on the anvil center rod.
Figure 59:
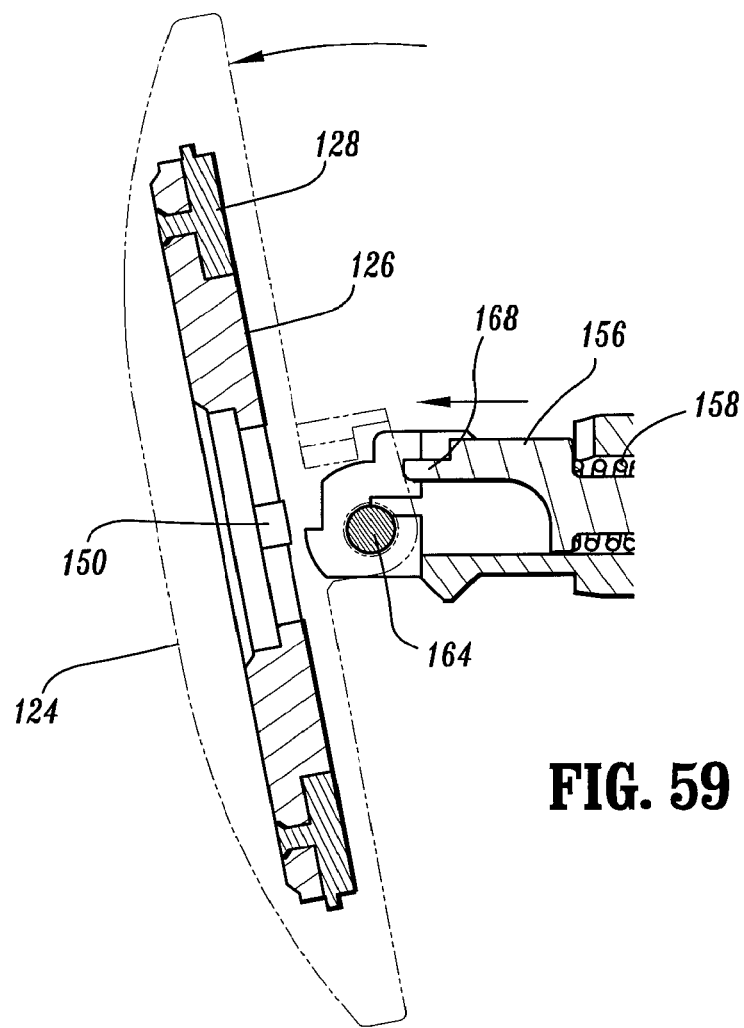
FIG. 59 is a side cross-sectional view of the anvil assembly shown in FIG. 56 as the anvil head assembly begins to tilt.
Figure 60:
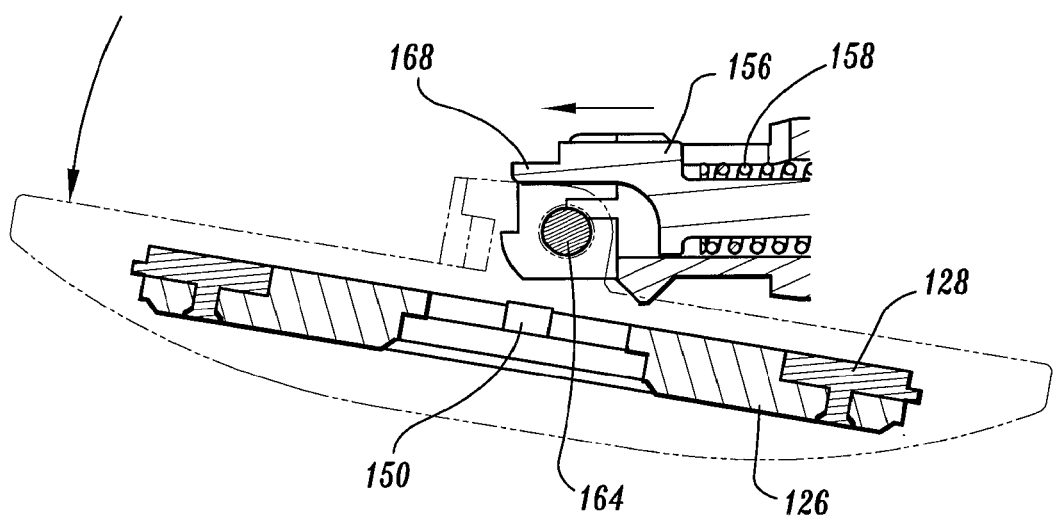
FIG. 60 is a side cross-sectional view of the anvil assembly shown in FIG. 59 with the anvil assembly tilted.
Figure 61:
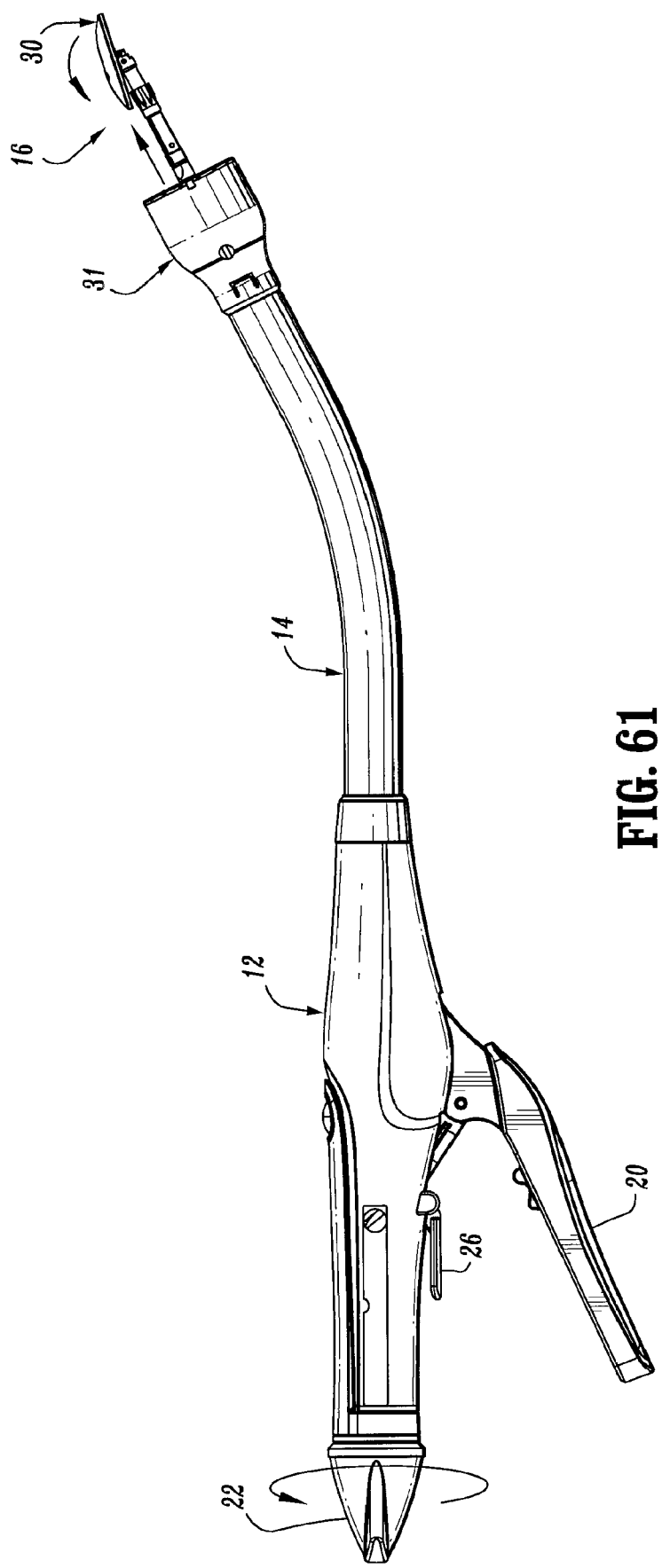
FIG. 61 is a side view of the surgical stapling device shown in FIG. 45 with the anvil head assembly unapproximated and tilted.

Cylindrical knife 188 is moved concurrently with pusher back 186 such that knife 188 moves into engagement with cutting ring 128 and backup plate 126. As discussed above, cutting ring 128 is preferably formed from polyethylene and backup plate 126 is preferably formed from metal. When knife 188 engages cutting ring 128, it cuts into cutting ring 128 and pushes backup plate 126 deeper into anvil head 124 to move tabs 150 (FIG. 56) from engagement with top surface 154a of center rod 154 (FIG. 56). Anvil head 124 is now free to pivot about member 164 and is urged to do so by plunger 156. It is noted that because the anvil assembly is in juxtaposed alignment with shell assembly 31, the anvil head 14 will not pivot fully until the anvil and shell assemblies have been unapproximated a distance sufficient to allow the anvil head to fully pivot. When backup plate 126 moves into anvil head 124, flexible arms 127a and 127b of retainer clip 127 (FIG. 55) spring outwardly to a position in front of backup plate 126 blocking movement of backup plate 126 out of anvil head 124. As discussed above, arms 127a and 127b prevent backup plate 126 from sticking to knife 188 when anvil assembly 30 is returned to the unapproximated position. Moreover, as discussed above, knife 188 may have a lubricious coating which prevents backup plate 126 and cut ring 128 from sticking to knife 188.

Figure 53:
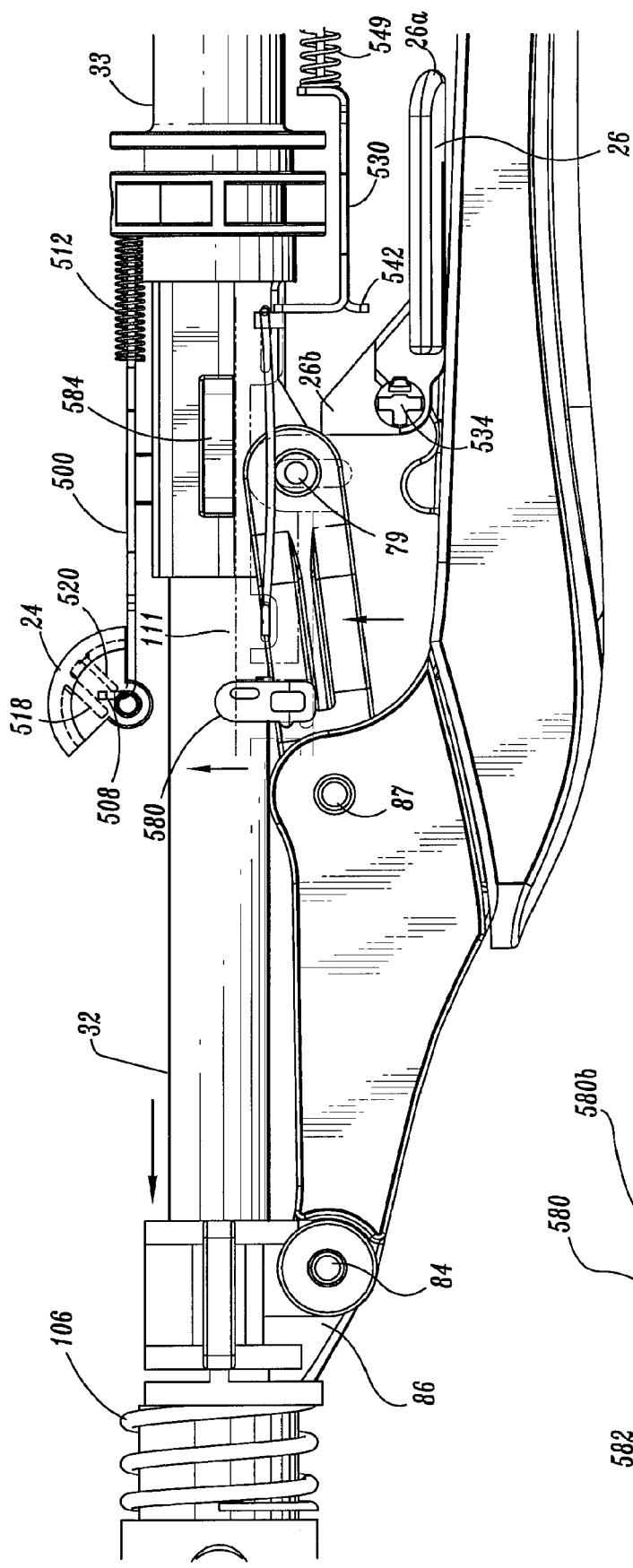
FIG. 53 is a side view of the handle assembly shown in FIG. 51 with the handle sections removed.
Figure 54:
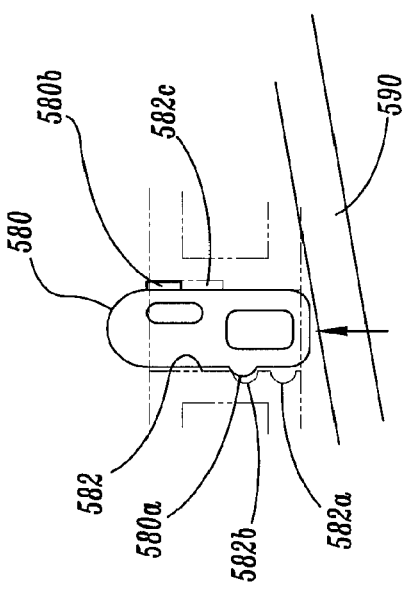
FIG. 54 is an enlarged view of the firing link extension engaging the abutment member of the tactile indicator mechanism of the handle assembly shown in FIG. 53.
Figure 58:
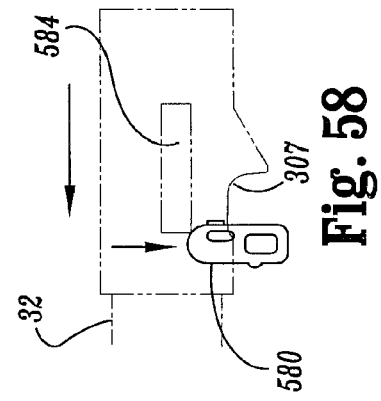
FIG. 58 is an enlarged view of the abutment member of the tactile indicator mechanism of the handle assembly shown in FIG. 53 (during unapproximation of the anvil and cartridge assemblies) with the wing of the screw stop, shown in phantom, in engagement with the abutment member.
Figure 55:
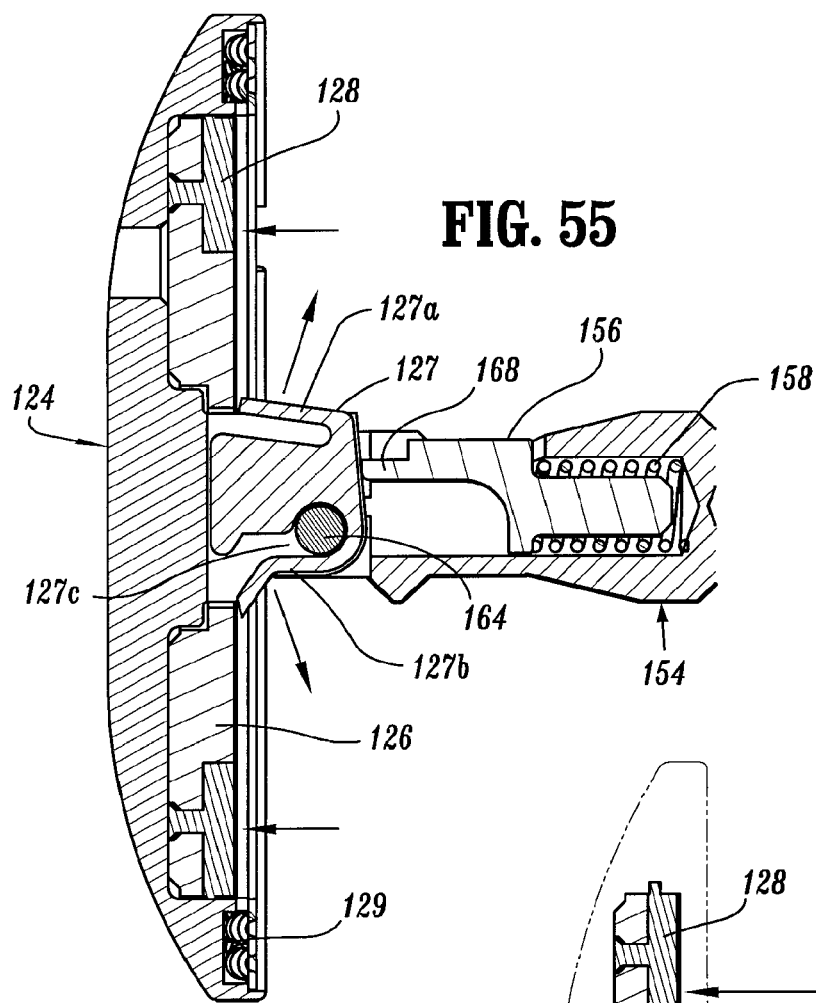
FIG. 55 is a side cross-sectional view of the distal portion of the anvil assembly of the surgical stapling device shown in FIG. 52.

Referring to FIGS. 53 and 54, as trigger 20 is actuated, i.e., compressed towards stationary handle 18, extension 590 of firing link 72 is pivoted towards and engages abutment member 580 to move abutment member 580 from its retracted to its extended position. In its extended position, abutment member 580 obstructs channel 111 of stationary handle 18.

Referring to FIGS. 57-60, during unapproximation of stapling device 10 after device 10 has been fired, wing 584 of screw stop 306 engages tactile indicator 580 (FIG. 58) at the point of unapproximation at which anvil head 124 is able to pivot to the tilted reduced profile position. Contact between wing 584 and tactile indicator 580 provides a tactile and/or audible indication that anvil head 124 has tilted. If additional force is provided to approximation knob 22, wing 584 of screw stop 306 will force tactile indicator to the retracted position to allow stapling device 10 to move to the fully open position. In this position, flexible arms 155 are positioned distally of bushing 209 and anvil assembly 30 can be disengaged from anvil retainer 28.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

For example, although the description refers exclusively to staples, it is envisioned that staples may include different types of tissue fasteners including two-part fasteners. In a stapling device for applying two-part fastener, the anvil assembly of the stapling device would support one part of each two-part fastener.

What is claimed is:

1. A surgical stapling device comprising a knife, said knife comprising a tissue cutting end and a surface, a portion of said surface having a coating thereon, the coating formed from a coating mixture comprising a first solution comprising at least one polydialkylsiloxane and a first organic solvent, and a second solution comprising at least one siliconization material and a second organic solvent, wherein the polydialkylsiloxane is present in the first solution at a concentration of from about 10 g/l to about 70 g/l and has a molecular weight sufficient to provide a viscosity of the coating mixture of at least about 10,000 cp, and the siliconization material is present in the second solution at a concentration of from about 10 g/l to about 80 g/l.

2. The surgical stapling device of claim 1 wherein the siliconization material comprises a polydimethylsiloxane having amino and alkoxy functional groups and the solvent is at least one of a hydrocarbon solvent of from about 5 to about 10 carbon atoms, a hydrofluoroether, and an alcohol.

3. The surgical stapling device of claim 1 wherein the first solution comprises a polydimethylsiloxane and the first solvent is at least one of a hydrocarbon solvent of from about 5 to about 10 carbon atoms and a hydrofluoroether.

4. The surgical stapling device of claim 1 wherein the first solution comprises a polydimethylsiloxane and the first solvent is selected from the group consisting of hexane and heptane.

5. The surgical stapling device of claim 1 wherein the second solution comprises an aminoalkyl siloxane and at least one other siloxane copolymerizable therewith and the second solvent is at least one of a hydrocarbon solvent of from about 5 to about 10 carbon atoms, a hydrofluoroether, and an alcohol.

6. The surgical stapling device of claim 1 wherein the second solution comprises a polydimethylsiloxane having amino and alkoxy functional groups and the second solvent is at least one of a hydrocarbon solvent of from about 5 to about 10 carbon atoms, a hydrofluoroether, and an alcohol.

7. The surgical stapling device of claim 1 wherein the second solution comprises a polydimethylsiloxane having amino and alkoxy functional groups and the second solvent is selected from the group consisting of hexane, heptane, isopropanol and mixtures thereof.

8. The surgical stapling device of claim 1 wherein the coating mixture further comprises a first solution comprising a polydimethylsiloxane and a hydrocarbon solvent selected from the group consisting of hexane and heptane and a second solution comprising a polydimethylsiloxane having amino and alkoxy functional groups and a solvent selected from the group consisting of hexane, heptane, isopropanol and mixtures thereof.

9. The surgical stapling device of claim 1, wherein the polydialkylsiloxane and siliconization material is prepared at a ratio of about 5:0.25.

10. The surgical stapling device of claim 1, wherein the polydialkylsiloxane and siliconization material is prepared at a ratio of about 2.5:0.5.

11. The surgical stapling device of claim 1, wherein the polydialkylsiloxane and siliconization material is prepared at a ratio of about 2:0.75.

12. The surgical stapling device of claim 1, wherein the polydialkylsiloxane is present in the first solution at a concentration of from about 35 g/l to about 45 g/l, and the siliconization material is present in the first solution at a concentration of from about 20 g/l to about 40 g/l.

13. The surgical stapling device of claim 1, wherein the coating mixture includes the first solution and the second solution at a ratio from about 12:1 to about 1:12.

14. The surgical stapling device of claim 1, wherein the coating mixture includes the first solution and the second solution at a ratio from about 6:1 to about 1:6.

15. The surgical stapling device of claim 1, wherein the coating mixture includes the first solution and the second solution at a ratio from about 2:1 to about 1:2.

16. A surgical stapling device for performing a circular anastomosis comprising:
a handle assembly including a firing trigger;
a body portion extending distally from the handle assembly;
a head portion including an anvil assembly and a shell assembly, the anvil assembly including a cutting ring and being movable in relation to the shell assembly between spaced and approximated positions, the shell assembly comprising:
a pusher movable in relation to the anvil assembly between retracted and extended positions, the pusher configured to eject staples; and
a circular knife comprising a tissue cutting end and a surface, the knife configured to engage and cut into the cutting ring upon firing, a portion of said surface and the tissue cutting end having a coating thereon to prevent the knife from sticking to the cutting ring, the coating formed from a coating mixture comprising at least one polydialkylsiloxane, at least one siliconization material, and at least one organic solvent, wherein the polydialkylsiloxane and siliconization material is prepared at a ratio of from about 5:0.25 to about 2:0.75, and the polydialkylsiloxane has a molecular weight sufficient to provide a viscosity of the coating mixture of at least about 10,000 cp.

17. The surgical stapling device of claim 16 wherein the siliconization material comprises a polydimethylsiloxane having amino and alkoxy functional groups and the solvent is at least one of a hydrocarbon solvent of from about 5 to about 10 carbon atoms, a hydrofluoroether, and an alcohol.

18. The surgical stapling device of claim 16 wherein the coating mixture further comprises a first solution comprising the polydialkylsiloxane and a first organic solvent and a second solution comprising the siliconization material and a second organic solvent.

19. The surgical stapling device of claim 18 wherein the first solution comprises a polydimethylsiloxane and the first solvent is at least one of a hydrocarbon solvent of from about 5 to about 10 carbon atoms and a hydrofluoroether.

20. The surgical stapling device of claim 18 wherein the first solution comprises a polydimethylsiloxane and the first solvent is selected from the group consisting of hexane and heptane.

21. The surgical stapling device of claim 18 wherein the second solution comprises an aminoalkyl siloxane and at least one other siloxane copolymerizable therewith and the second solvent is at least one of a hydrocarbon solvent of from about 5 to about 10 carbon atoms, a hydrofluoroether, and an alcohol.

22. The surgical stapling device of claim 18 wherein the second solution comprises a polydimethylsiloxane having amino and alkoxy functional groups and the second solvent is at least one of a hydrocarbon solvent of from about 5 to about 10 carbon atoms, a hydrofluoroether, and an alcohol.

23. The surgical stapling device of claim 18 wherein the second solution comprises a polydimethylsiloxane having amino and alkoxy functional groups and the second solvent is selected from the group consisting of hexane, heptane, isopropanol and mixtures thereof.

24. The surgical stapling device of claim 16 wherein the coating mixture further comprises a first solution comprising a polydimethylsiloxane and a hydrocarbon solvent selected from the group consisting of hexane and heptane and a second solution comprising a polydimethylsiloxane having amino and alkoxy functional groups and a solvent selected from the group consisting of hexane, heptane, isopropanol and mixtures thereof.

* * * * *